US012359948B2

(12) United States Patent
Elkins et al.

(10) Patent No.: US 12,359,948 B2
(45) Date of Patent: Jul. 15, 2025

(54) PORTABLE GAS MONITOR

(71) Applicant: Elkins Earthworks, LLC, Wadsworth, OH (US)

(72) Inventors: Charles Daniel Elkins, Wadsworth, OH (US); David Ernest Walder, Wadsworth, OH (US); Holden Chase Leblanc, Wadsworth, OH (US); Steve Woodrow Smith, Wadsworth, OH (US); Daniel Dwayne Duncan, Wadsworth, OH (US)

(73) Assignee: Elkins Earthworks, LLC, Wadsworth, OH (US)

( * ) Notice: Subject to any disclaimer, the term of this patent is extended or adjusted under 35 U.S.C. 154(b) by 288 days.

(21) Appl. No.: 17/975,183

(22) Filed: Oct. 27, 2022

(65) Prior Publication Data
US 2023/0135269 A1 May 4, 2023

Related U.S. Application Data

(60) Provisional application No. 63/272,756, filed on Oct. 28, 2021.

(51) Int. Cl.
*G01D 21/02* (2006.01)

(52) U.S. Cl.
CPC ................... *G01D 21/02* (2013.01)

(58) Field of Classification Search
CPC .......... B09B 1/00; B09B 1/006; B09B 1/008; E21B 47/06; E21B 49/08; E21B 47/07; E21B 49/0875; E21B 47/10; E21F 7/00; G05B 2219/41108; G08B 21/182; G08B 21/12; G01D 21/02; G01F 15/08; G01F 15/002; G01F 15/005; G01F 15/063; G01J 3/0272; G01N 33/0004; G01N 33/0047; G01N 33/005; G01N 33/004; G01N 33/0044; G01N 33/0036; G01N 33/0075; G01N 2201/0221; G01N 21/35; G01N 21/474; G01N 21/94; G01N 33/0009; G01N 21/534; G01N 2291/0217; G01N 2291/0256; G01N 1/26; G01N 33/0073; G01V 11/002; G01V 9/007
See application file for complete search history.

(56) References Cited

U.S. PATENT DOCUMENTS

| 5,063,519 | A | 11/1991 | Zison |
| 5,616,841 | A | 4/1997 | Brookshire |
| 6,085,576 | A * | 7/2000 | Sunshine ........... G01N 33/0031 340/634 |
| 6,169,962 | B1 | 1/2001 | Brookshire |
| 6,356,205 | B1 | 3/2002 | Salvo et al. |

(Continued)

FOREIGN PATENT DOCUMENTS

| EP | 1217420 | 6/2022 |
| GB | 2273593 | 6/1994 |
| WO | 1993011421 | 6/1993 |

*Primary Examiner* — Daniel R Miller
*Assistant Examiner* — Eric Sebastian Von Wald
(74) *Attorney, Agent, or Firm* — UB Greensfelder LLP; Brian E. Turung

(57) ABSTRACT

A portable monitor used to measure landfill gas, landfill well parameters, and/or gas from a well, biogas facility, subterranean location, and any other testing location. The portable fluid monitor is particularly useful in measuring gas pressures and compositions of gases.

20 Claims, 9 Drawing Sheets

(56) References Cited

U.S. PATENT DOCUMENTS

| | | |
|---|---|---|
| 6,579,231 B1 | 6/2003 | Phipps |
| 6,658,915 B2 | 12/2003 | Sunshine et al. |
| 6,999,883 B1 * | 2/2006 | Brady .................. G05D 7/0635 |
| | | 702/50 |
| 2001/0005812 A1 | 6/2001 | Brookshire et al. |
| 2001/0039824 A1 | 11/2001 | Sunshine et al. |
| 2003/0206834 A1 | 11/2003 | Chiao et al. |
| 2004/0083797 A1 | 5/2004 | Ward et al. |
| 2004/0170409 A1 | 9/2004 | Faries et al. |
| 2004/0267340 A1 | 12/2004 | Cioanta et al. |
| 2005/0034644 A1 | 2/2005 | Hamm |
| 2005/0061067 A1 | 3/2005 | Sunshine et al. |
| 2005/0120775 A1 | 6/2005 | Grayfer et al. |
| 2005/0236042 A1 | 10/2005 | Hansen |
| 2008/0127726 A1 * | 6/2008 | Elkins .................... E21B 47/00 |
| | | 73/152.42 |
| 2009/0133479 A1 | 5/2009 | Haberland |
| 2010/0057401 A1 | 3/2010 | Scheffler et al. |
| 2011/0096332 A1 | 4/2011 | Bugge |
| 2022/0008973 A1 * | 1/2022 | Quigley ............. G01N 33/0044 |
| 2024/0027338 A1 * | 1/2024 | Vidal ....................... G01F 1/46 |

* cited by examiner

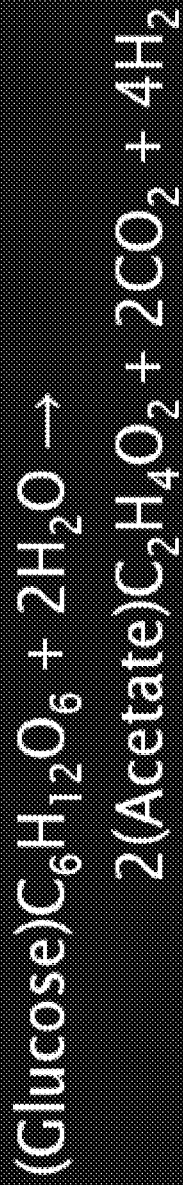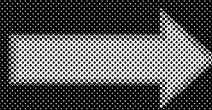
FIG. 6

PORTABLE GAS MONITOR

The present disclosure claims priority on U.S. Provisional Application Ser. No. 63/272,756 filed Oct. 28, 2021, which is incorporated herein by reference.

The present disclosure is directed to portable fluid monitoring systems, particularly to a portable fluid monitoring system used to measure fluid pressure and/or fluid composition, and even more particularly to a portable gas monitoring system used to measure gas pressures and compositions of gases at a plurality of different sample location (e.g., well, landfill well, biogas facility, subterranean location, any other testing location). The portable fluid monitor is particularly useful in measuring gas pressures and compositions of gases from landfill wells; however, the portable fluid monitor can be used for other or additional applications.

BACKGROUND OF THE DISCLOSURE

Landfills are commonly formed by depositing municipal solid waste and many other types of trash in a canyon or pit (or even on flat ground) and depositing soil on top of the solid waste and trash. It is common for there to be alternating layers of trash and soil, one atop another in the landfill. The waste and soil layers are individually and collectively porous media through which gas may readily flow. Once municipal waste is disposed of at a landfill, the organic portion of the waste begins to decompose. This decomposition initially proceeds through an aerobic biodegradation process wherein much of the available oxygen in the buried waste is consumed. This decomposition produces end products which are primarily carbon dioxide and water. After a while, usually ranging from a few weeks to several months, the waste consumes essentially all the free oxygen in the landfill. The decomposition of the waste then proceeds through an anaerobic biodegradation process. During the anaerobic decomposition of the waste, microbes break down the cellulose and other organic wastes to produce methane ($CH_4$) and carbon dioxide ($CO_2$). The landfill gas (LFG) that is formed typically includes about 55% methane, 44% carbon dioxide, and less than 1% trace gas. The trace gases consist of a wide variety of volatile compounds, which vary depending on the particular landfill. However, some landfills generate high levels of hydrogen gas and can generate other gases, such a carbon monoxide and hydrogen sulfide.

Landfill gas well extraction systems are commonly used to control landfill gas surface emissions, control landfill gas subsurface migration away from the landfill, and often to collect landfill gas for energy recovery. These extraction systems typically include one or more vertical and/or horizontal landfill gas extraction wells in fluid communication with one or more header piping systems. The header piping system is, in turn, fluidly connected to a vacuum source (e.g., centrifugal blower, etc.).

Normal monitoring frequency for a complete field monitoring session with full field readings varies from typically every several months to once a week. Wellfield monitoring should not normally be extended beyond one month. Typical field readings for each well include a) name of field tester, b) location of landfill well, c) date/time of readings of landfill well, d) landfill gas composition (e.g., methane, oxygen, carbon dioxide, nitrogen, etc.), e) wellhead gas temperature, f) ambient air temperature, g) static pressure of wellhead, h) applied vacuum pressure in wellhead, i) wellhead gas flow, j) wellhead adjustment valve position, k) new wellhead vacuum and flow information after any flow rate adjustment, l) calculation of landfill gas flow rate and methane flow rate; and m) comments and/or notes regarding well, landfill, testing procedure, etc. Other types of gases in the landfill gas may be tested (e.g., carbon monoxide, hydrogen sulfide, hydrogen, oxygen, etc.).

A portable gas monitor is commonly used to measure gas concentrations from a landfill. The equipment cost, equipment maintenance, and personnel costs for constantly monitoring a gas well is generally too expensive and unnecessary to properly monitor a landfill well. The composition of the extracted landfill gas and the pressure in the well is measured periodically (e.g., daily, weekly, monthly, etc.). Generally, a landfill well is monitored every month, three months, six months or twelve months depending on local, state, and federal regulations, the size of the well, and/or the location of the well and the gas volume flowing from the well. These portable monitors are carried to a landfill or landfill well, temporarily connected to the landfill well, measure information from the connected landfill well, are disconnected from the landfill well, carried to another landfill well on a same or different landfill, temporarily connected to the new landfill well, measure information from the connected to new landfill well, disconnected from the new landfill well, etc. This process is repeated for each different landfill being measured by the portable monitor.

Landfill gas instruments were originally configured to measure methane ($CH_4$) and $CO_2$, the principal byproducts of methanogenesis, along with oxygen as the primary limiting agent that impacted the anaerobic process. However, the biochemical process is more complex than just the end products of methanogenesis, with many stages that can be interrupted and cause a change in gas composition.

There has been the need for the measurement of hydrogen in landfills for years. Hydrogen becomes present in landfills during the acid phase of landfill gas generation and is part of the normal fermentation process, namely (Glucose) $C_6H_{12}O_6+2H_2O \rightarrow 2$ (Acetate) $C_2H_4O_2+2\ CO_2+4H_2$, and then fermentation then leads to methanogenesis $4H_2+CO_2 \rightarrow CH_4+2H_2O$ (See FIG. 6).

During the normal acidogenesis (Phase II), the hydrogen content in the gas from the landfill can increase up to approximately 20% (as illustrated in FIG. 8). During normal methanogenesis (as illustrated in Phase III of FIG. 8), the hydrogen levels decrease and are typically measured at levels less than 1% as methanogenesis begins. Measuring hydrogen during normal anaerobic conditions can provide the user with an understanding of how the biochemical process is progressing within Phase III, ultimately culminating in principally $CH_4$ and $CO_2$.

Over the past 10 to 15 years, the solid waste industry has found that several landfill owners/operators are reporting sustained elevated gas temperatures exceeding expected temperatures during normal methanogenic conditions. These elevated temperature landfills (ETLFs) often exhibit a decline in methane generation and the increased production of hydrogen and $CO_2$, suggesting that the acidogenesis or acetogenesis phases are the prevailing process when gas temperatures are elevated. The cause and effect are not well understood for the process changes, which makes the measurement of $H_2$ an important tool for landfill owner/operators.

Elevated temperature landfill reactions occur deep within landfills where the waste is typically very wet and saturated and where oxygen is typically non-existent. Both factors basically rule out the presence of combustion and subsurface oxidation.

The reaction associated with an ETLF slowly increases the concentration of $H_2$ and CO within the extracted gases.

At the start of such ETLF reaction, the concentration of $H_2$ that is measured in the landfill gas can be measured in parts per million (PPM). However, as the ETLF reaction progresses, the amount of $H_2$ in the landfill gas increases above 1 vol. % of the landfill gas and can be up to or even exceed 30 vol. % of the landfill gas. There is some consensus in the industry that increased concentrations of hydrogen gas in the landfill gas is an indication of an imbalance in the microbial population in the landfill. There is some evidence that increased concentrations of hydrogen in the landfill gas is an indicator that the landfill gas production is stalling, which can potentially lead to ETLFs.

Although the measurement of elevated levels of hydrogen in landfill gas can be beneficial to the monitoring of the landfill, measurement of hydrogen gas above the ppm levels using conventional landfill gas monitors is difficult. Conventional landfill gas monitors typically do not measure hydrogen levels in the landfill gas. Also, it has been found that high levels of hydrogen in the landfill gas can result in false readings for carbon monoxide and hydrogen sulfide when the hydrogen in the landfill gas exceeds 1-2 vol. %.

In view of the deficiencies that exist in prior art portable monitors for landfill wells, there is a need for a portable monitor that simplifies the testing of landfill wells and which overcomes the past deficiencies of prior art portable monitors.

SUMMARY OF THE DISCLOSURE

The present disclosure is directed to an improved portable monitor that can be used to measure one or more properties (e.g., flow rate, temperature, composition, pressure, LEL, etc.) of a fluid stream (e.g., gas and/or liquid stream from a well, biogas facility, etc.). The portable monitor is particularly adapted for use with measuring one or more properties of fluid (e.g., gas, liquid) from a well such as, but not limited to, a landfill well; however, it will be appreciated that the portable monitor can be used to measure one or more properties of the fluid in other types of applications (e.g., measure the fluid composition/temperature/pressure/LEL in a cave, measure fluid composition/temperature/pressure/LEL in a sewage system, measure fluid composition/temperature/pressure/LEL in a refinery, biogas plants and other biogas-generating facilities, etc.). The portable monitor is adapted for indoor and outdoor use.

The portable monitor is configured to monitor and measure fluids from one or more wells, biogas facilities, etc. The portable monitor is generally configured to only measure one well or facility at a time, then be disconnected from the well or other testing location. and then subsequently be reconnected to another well or other testing location for taking measurements from such other well or facility. The portable monitor is also not configured to be part of an automated control system for a well or at a certain facility (e.g., biogas facility, etc.). The portable monitoring system is connected and/or disconnected to a well or testing location by a user, robot, drone, unmanned vehicle, etc. Generally, the portable monitor is disconnected from the well or testing location once the readings for the well or testing location have been obtained. When the portable monitoring system is used to test a well, the information about the well that is measured by the portable monitor can then be used by an operator to adjust the flow rate of fluids from the well. Such adjustments to the well by the user can be manual or can be input by the user into a control system. As can be appreciated, information from the portable monitor can be downloaded into another device that can then use the information from the portable monitor to control the well. The portable monitor of the present disclosure is not generally configured to provide constant control of the well; however, this is not required. The portable monitor is primarily configured to be connected to a well or testing location (e.g., biogas facility, etc.) during periodic time periods (e.g., hourly, daily, weekly, monthly, quarterly, semi-annually, yearly, etc.) to take periodic measurements of the well or testing location, then be disconnected from the well or testing location.

The portable monitor is made of durable materials to withstand the outside elements (e.g., rain, cold weather, strong winds, snow, dust, sun, etc.). The portable monitor also has a size, shape, and weight that enables a user to easily and conveniently carry the portable monitor to a testing site (e.g., landfill well, etc.). Typically, the portable monitor has a total weight of less than about 20 lbs., typically less than about 10 lbs., and more typically less than about 6 lbs. The portable monitor also typically has a total volume of less than about 500 cubic inches, typically less than about 400 cubic inches, and more typically less than about 250 cubic inches. The portable monitor is configured to be used in a variety of environments. A carrying device (e.g., backpack, brief case, drone, robot, unmanned vehicle, etc.) can optionally be used to conveniently store and/or transport the complete portable monitor; however, this is not required. As can be appreciated, the portable monitor can be carried by hand by a user to a test site.

In one non-limiting aspect of the present disclosure, the portable monitor optionally includes a plurality of pressure sensors. As can be appreciated, the portable monitor can include no pressure sensors or can include one or more pressure sensors. In one non-limiting embodiment of the disclosure, the portable monitor optionally includes three or more pressure sensors. The three or more pressure sensors enable the portable monitor to simultaneously measure three or more different pressures. For example, when the portable monitor is used to measure pressures on a gas well wherein gas is being drawn by a vacuum (e.g., landfill well, etc.), the three or more pressure sensors enable an operator to simultaneously measure the static or applied vacuum pressure on the well, the impact or differential pressure on the well, and the available vacuum or header pressure that can be applied to the well. Prior art portable monitors for landfill wells only included two pressure sensors. These two pressure sensors measured the applied vacuum pressure or static vacuum of the well. As such, if an operator wanted to measure the available vacuum pressure of the well, the operator had to disconnect one of the tubes from the applied vacuum port on the well and reconnect the tube at an available pressure vacuum port on the well. This procedure was not only time consuming and inconvenient (especially in inclement weather) but the accuracy of the data readings potentially could be compromised during the disconnecting and reconnecting of the vacuum tubes. These problems associated with prior portable monitors are overcome by the portable monitor of the present disclosure. The portable monitor of the present disclosure enables an operator to connect the portable monitor of the present disclosure to all three pressure ports on a well so the applied or static vacuum pressure, the differential pressure, and the available vacuum pressure of the well can be determined without having to further reconnect and disconnect vacuum tubes. As can be appreciated, more than three pressure sensors can be included on the portable monitor.

In another and/or additional non-limiting aspect of the present disclosure, the portable monitor is optionally a multi-unit system. As can be appreciated, the portable monitor can be a single unit. In one non-limiting embodiment of the disclosure, the portable monitor optionally includes a separate control unit and a separate measuring unit. The measuring unit of the portable monitor of the present disclosure can be optionally configured to be connected to various portions of a well or testing location to measure one or more parameters of the well or testing location. The control unit of the portable monitor of the present disclosure can be configured to provide instructions and/or commands to the measuring unit of the portable monitor, and/or to receive information from the measuring unit of the portable monitor. As such, an operator is able to 1) remotely monitor the operation of the measuring unit of the portable monitor, 2) remotely control one or more operations of the measuring unit of the portable monitor, 3) remotely review information that is tested and/or measured by the measuring unit of the portable monitor, and/or 4) remotely process information receive from the measuring unit of the portable monitor. In one non-limiting use of the portable monitor, the multi-unit configuration of the portable monitor enables an operator to 1) first temporarily connect the measuring unit of the portable monitor at or near the well or testing location, and connect the required tubes, wires, etc., to the measuring unit of the portable monitor, and 2) then use the control unit of the portable monitor to begin the required operations of the measuring unit of the portable monitor and acquire all of the required data from the measuring unit of the portable monitor from a remote location. The measuring unit of the portable monitor and control unit of the portable monitor can communicate between one another wirelessly (e.g., IR connection, RF connection, Bluetooth®, mobile phone connection, WiFi connection, microwave connection, broadcast radio connection, satellite connection, etc.) and/or through a cable connection (fire wire connection, USB connection, serial cable, ethernet cable, any type of data cable, etc.). This wireless configuration allows an operator to make adjustments from remote locations and also enables the operator to see how such adjustments effect the well being monitored without having to walk back and forth between the monitor and the well or testing location. The wireless connection enables an operator to be located in a remote location (e.g., vehicle, power plant control room, sheltered area, header valve on the well, etc.) during the testing of the well or testing location. This configuration of the portable monitor enables an operator to connect the measuring unit of the portable monitor to a well or testing location and then move to a sheltered area or other remote location (e.g., other regions on the well, etc.) to operate and/or monitor operation of the measuring unit of the portable monitor. As such, during inclement weather conditions, operators only have to expose themselves to such conditions during the setting up and dismantling of the measuring unit of the portable monitor on the well or testing location. The testing period of the well or testing location can then be accomplished in a protected or sheltered area. In situations wherein a wireless connection cannot be created and/or is not desired by the operator, a cable connection can be connected between the control unit and the measuring unit of the portable monitor. Even with use of a cable connection, the operator can operate/monitor the measuring unit of the portable monitor from the control unit of the portable monitor in a more convenient manner (e.g., sit in a chair, sit on an ATV, sit in a car, SUV truck, etc., located close to the measuring unit of the portable monitor, etc.). In another non-limiting embodiment, the control unit can optionally be a portable smart device (e.g., smart phone, tablet, laptop computer, etc.) that includes an app or programs that enables the portable smart device to function as the control unit when the user is using the app or software program to communicate with the measuring unit.

In another and/or additional non-limiting aspect of the present disclosure, the portable monitor includes one or more pressure sensors, fluid pumps, and/or chemical analyzers. The portable monitor can also optionally include one or more heating elements or pads, and/or thermocouples. The portable monitor can optionally include one or more microprocessors and software and/or firmware to calculate one or more properties of fluid analyzed from a well or testing location. When the portable monitor optionally includes a control unit and a measuring unit, the control unit can optionally include one or more microprocessors and software and/or firmware to partially or fully calculate one or more properties of fluid analyzed from a well or testing location based on data sent from the measuring unit of the portable monitor to the control unit of the portable monitor. In one non-limiting embodiment of the disclosure, when the control unit of the portable monitor is a separate unit from the measuring unit of the portable monitor, the control unit of the portable monitor optionally does not include pressure sensors, fluid pump(s), temperature sensors, fluid intake ports, fluid exhaust ports, and/or chemical analyzers, and such components are located in the measuring unit. In another and/or alternative non-limiting embodiment, when the control unit of the portable monitor is a separate unit from the measuring unit, the control unit of the portable monitor optionally does not include one or more heating elements or pads and/or and thermocouples, and the measuring unit optionally includes such components. In another and/or alternative non-limiting embodiment, when the control unit of the portable monitor is a separate unit from the measuring unit, the control unit of the portable monitor and/or the measuring unit of the portable monitor can optionally include wireless and/or wired communication capabilities.

In another and/or additional non-limiting aspect of the present disclosure, the portable monitor is optionally configured to provide geographic location information. In one non-limiting embodiment of the disclosure, when the control unit of the portable monitor is a separate unit from the measuring unit of the portable monitor, the measuring unit of the portable monitor and/or control unit of the portable monitor optionally includes a GPS component that provides GPS location information. Many wells or testing location are located in remote locations. Furthermore, on some landfill sites or testing sites, multiple landfill wells or testing locations exist. The use of GPS can be used to confirm the location of the proper landfill well or testing location to be tested, and/or locate the landfill well or testing location to be tested. The GPS location function on the portable monitor can be used to easily identify which well or testing location was tested and the exact location of a well or testing location that was tested and/or is to be tested. In one non-limiting aspect of this embodiment, the control unit includes a GPS component that provides GPS location information. In another non-limiting aspect of this embodiment, the measuring unit of the portable monitor includes a GPS component that provides GPS location information.

In another and/or additional non-limiting aspect of the present disclosure, the portable monitor has a durable configuration. In one non-limiting embodiment of the disclosure, the portable monitor is configured to be used in a wide variety of environments. When in use, the portable monitor may be exposed to high temperatures, low temperatures, rain, snow, ice, fog, dust, etc. The housing of the portable monitor can optionally be configured to protect the internal components from such environmental conditions. In one non-limiting aspect of this embodiment, the portable monitor optionally has an Ingress Protection Rating for dust of at least 4, typically at least 5, and more typically 6; and an Ingress Protection Rating for water of at least 3, more typically at least 4, even more typically at least 5, still more typically at least 6, and still even more typically at least 7. In one non-limiting configuration of the portable monitor, the Ingress Protection Rating for the measuring unit is optionally at least IP43, typically at least IP55, and more typically at least IP67. Such IP rating enables the measuring unit to be used in rainy conditions, snowy conditions, sunny conditions, dusty condition, etc., and still operate properly. In another and/or alternative non-limiting aspect of this embodiment, the portable monitor is optionally configured so that it can properly operate in temperatures at least as low as about 32° F. more typically at least as low as about 0° F., and even more typically at least as low as about −20° F., and in temperatures at least as high as about 90° F., typically at least as high as about 120° F., and more typically at least as high as about 140° F. In another and/or alternative non-limiting embodiment of the disclosure, the housing of the portable monitor is optionally made of a durable material that protects the internal components of the portable monitor from damage when the measuring unit falls from a well or testing location and/or is inadvertently dropped on the ground. The one or more materials used to at least partially form the housing can include, but are not limited to, metal, plastic, rubber, fiber- and/or carbon-reinforced material, etc. When the portable monitor includes a control unit and a measuring unit, the housing of the measuring unit can optionally be made to be more durable than the control unit. As such, the measuring unit can optionally have the protection rating and durability and temperature endurance as discussed above, but the control unit may not have reduced protection rating and durability and temperature endurance as comparted to the measuring unit.

In another and/or additional non-limiting aspect of the present disclosure, the portable monitor can optionally be used to calculate the flow rate of fluid to/from a landfill or testing location. In one non-limiting embodiment, the portable monitor can be optionally configured to use the detection/measurement of one or more pressures to calculate the flow rate of fluid at or near the location of the detected pressures. In one particular non-limiting configuration, the portable monitor can be configured to calculate the flow rate of gas to/from a landfill or testing location based at least partially on one or more pressures detected/measured by the portable monitor. As can be appreciated, the portable monitor can be used to calculate the flow rate of other or additional fluids based at least partially on one or more pressures detected/measured by the portable monitor. As can be appreciated, the measurement of gas flow rate can be detected by other or additional arrangements (e.g., measure fluid velocity, electromagnetic flow meters, vortex time flow meter, paddle wheel flow meter, thermal dispersion flow sensor, floating element flow sensor, direct mass flow meters, positive displacement flow meters, etc.).

In another and/or additional non-limiting aspect of the present disclosure, the portable monitor can include one or more chemical analyzers to identify and/or measure the concentration of one or more components in a fluid stream (e.g., landfill gas, biogas facility, cave, down-well site, etc.). In one non-limiting aspect of the present disclosure, the portable monitor can include one or more chemical analyzers to identify and/or measure the concentration of one or more components in a fluid stream and/or sample. In one particular non-limiting configuration, the portable monitor can be used to identify gases and/or measure gas concentration from a landfill well or testing location. In such a configuration, the portable monitor includes one or more chemical analyzers configured to identify and/or measure the concentration of one or more of methane, carbon dioxide, hydrogen, hydrogen sulfide, carbon monoxide, chlorine, cyanide, mercaptan, nitric oxides, nitrogen, sulfur oxides, ammonia, ammonium, and oxygen. In one non-limiting configuration, the portable monitor includes a plurality of sensors to simultaneously measure the concentration of two or more components in the fluid from the landfill well or testing location. In such a configuration, the portable monitor can, but is not required to, include two or more separate chemical analyzers. In another non-limiting configuration, the portable monitor includes a plurality of sensors to simultaneously measure the concentration of three or more components in the fluid from the landfill well or testing location. In such a configuration, the portable monitor can, but is not required to, include three or more separate chemical analyzers. In still another non-limiting configuration, the portable monitor includes a plurality of sensors to simultaneously measure the concentration of four or more components in the fluid from the landfill well or testing location. In such a configuration, the portable monitor can, but is not required to, include four or more separate chemical analyzers. When the portable monitor is configured to measure the concentration of two components in the fluid, such components generally include two components selected from the group of carbon dioxide, carbon monoxide, hydrogen, hydrogen sulfide, methane, and oxygen. When the portable monitor is configured to measure the concentration of three components in the fluid, such components generally include three components selected from the group of carbon dioxide, carbon monoxide, hydrogen, hydrogen sulfide, methane, and oxygen. When the portable monitor is configured to measure the concentration of four components in the fluid, such components generally include four components selected from the group of carbon dioxide, carbon monoxide, hydrogen, hydrogen sulfide, methane, and oxygen. When the portable monitor is configured to measure the concentration of five components in the fluid, such components generally include five components selected from the group of carbon dioxide, carbon monoxide, hydrogen, hydrogen sulfide, methane, and oxygen. The one or more chemical analyzers used to identify and/or measure gas concentration can be configured to be replaceable in the portable monitor so the portable monitor can be customized by the operator; however, this is not required. As can also be appreciated, when the portable monitor is configured for uses other than or in addition to measuring landfill gas or gas from a testing location, the portable monitor can include chemical analyzers configured to measure the desired gases and/or liquids in a tested fluid stream. In another and/or additional non-limiting aspect of this embodiment, one or more chemical analyzers in the portable monitor can include analyzers such as, but not limited to, IR measuring cells, galvanic cells, tunable diode laser, thermoconductivity cells, FTIR, etc. In still another and/or additional non-limiting aspect of this embodiment, the portable monitor can optionally include one or more chemical analyzers to measure the lower explosive limit (LEL) and/or upper explosive limit (UEL) of one or more components in a fluid stream. As can be appreciated, a separate chemical analyzer may not be required to measure the lower explosive limit (LEL) and/or upper explosive limit (UEL) of one or more components in a fluid stream if the information from the other chemical analyzers is used to calculate the lower explosive limit (LEL) and/or upper explosive limit (UEL) of one or more components in a fluid stream via a microprocessor or the like. In one particular non-limiting configuration, the portable monitor measures the LEL and/or UEL of methane in a fluid stream. For methane, the LEL is at about 5% and the UEL is about 15%. This LEL and/or UEL reading can be useful for the operator of the portable monitor. At concentrations in air below the LEL, there is not enough explosive component (e.g., methane, hydrogen, etc.) to continue an explosion; whereas at concentrations above the UEL the explosive component has displaced so much air that there is not enough oxygen to begin an explosive reaction. As can be appreciated, the LEL and/or UEL reading can be determined by the portable monitor for other or additional explosive components. In another and/or alternative non-limiting embodiment, when the control unit of the portable monitor is a separate unit from the measuring unit, the one or more chemical analyzers are located in the measuring unit.

In another and/or additional non-limiting aspect of the present disclosure, the portable monitor can optionally include one or more pumps to draw fluid into and/or expel fluid out of the portable monitor. In one non-limiting configuration, at least one pump is used to draw landfill gas or gas from a testing location through one of the pressure sensors in the portable monitor so the gas can then be directed to one or more chemical analyzers in the portable monitor. In another and/or alternative non-limiting embodiment, when the control unit of the portable monitor is a separate unit from the measuring unit, the measuring unit of the portable monitor includes one or more pumps.

In another and/or additional non-limiting aspect of the present disclosure, the portable monitor can optionally include one or more temperature ports to receive temperature information from one or more temperature probes. The temperature measurement can be used to facilitate in flow rate calculations, provide information on the activity of a landfill, testing location, etc. In one non-limiting aspect of this embodiment, the portable monitor includes at least one temperature port configured to be connected to a temperature probe that is in turn connected to a temperature monitoring port of a landfill well or testing location. The temperature probe can be configured to measure the temperature of the landfill gas or gas at a testing location. The portable monitor can optionally include one or more temperature sensors to measure the gas sensor temperatures and/or the gas supplied to the gas sensor. These temperatures can be optionally used in equations, tables, etc., to make the gas measurement by the one or more gas sensors more accurate. In another and/or alternative non-limiting embodiment, when the control unit of the portable monitor is a separate unit from the measuring unit, the measuring unit of the portable monitor includes one or more temperature ports.

In another and/or additional non-limiting aspect of the present disclosure, the portable monitor can optionally include one or more indicators to facilitate in the use and/or operation of the portable monitor. Such indicators can include, but are not limited to, heater activation/deactivation indicator, battery level indicator, battery charge indicator, battery use indicator, on/off indicator, coupler/port indicator to indicate when coupler/port is properly and/or improperly connected, coupler/port indicator to indicate when coupler/port is in use, malfunction indicator, carbon filter indicator to indicate when a carbon filter or gas stripping filter is spent (e.g., indicator based on a timer, indicator based on an optical sensor, indicator based on an electrical sensor, etc.), error and/or warning indicator, etc. The one or more indicators can be in a variety of forms such as, but not limited to, a sound indicator, a visual indicator (LED light, LCD light or panel, incandescent light, etc.), etc. In another and/or additional non-limiting embodiment of the disclosure, the portable monitor can include one or more monitors/displays (e.g., LCD panel, etc.) to enable an operator to view/use one or more operations and/or functions of the portable monitor, enable an operator to control one or more operations and/or functions of the portable monitor, view one or more indicators for the portable monitor, etc. The one or more monitors/displays can optionally be a touch-screen monitor/display. In another and/or alternative non-limiting embodiment, when the control unit of the portable monitor is a separate unit from the measuring unit, the control unit of the portable monitor and/or the measuring unit of the portable monitor can include one or more indicators, and/or one or more monitors/displays.

In another and/or additional non-limiting aspect of the present disclosure, the portable monitor can optionally include one or more buttons and/or switches. The one or more buttons and/or switches can be used to enable an operator to activate and/or deactivate one or more functions of the portable monitor, to display and/or access information from the portable monitor, to provide instructions and/or information to the portable monitor, turn on/turn off the portable monitor, etc. In another and/or alternative non-limiting embodiment, when the control unit of the portable monitor is a separate unit from the measuring unit, the control unit of the portable monitor and/or the measuring unit of the portable monitor can include one or more buttons and/or switches.

In another and/or additional non-limiting aspect of the present disclosure, the portable monitor can optionally include a power pack compartment to store one or more energy cells. The one or more energy cells can be used to provide power to one or more components of the portable monitor. The power pack compartment can be configured to enable easy access for servicing and/or replacement of one or more energy cells; however, this is not required. The power pack compartment can include a power port to enable one or more of the energy cells to be recharged while contained in the power pack compartment; however, this is not required. In another and/or alternative non-limiting embodiment, when the control unit of the portable monitor is a separate unit from the measuring unit, the control unit of the portable monitor and/or the measuring unit of the portable monitor can include one or more power packs.

In another and/or additional non-limiting aspect of the present disclosure, the portable monitor can optionally include one or more connection ports used to a) connect the measuring unit of the portable monitor to the control unit of the portable monitor to enable data transfer between the two units when the portable monitor optionally includes a control unit and a measuring unit, b) connect the portable monitor to a phone jack, c) connect the portable monitor to an ethernet connector, d) connect the portable monitor to another computer, and/or e) connect the portable monitor to a computer, data storage device, and/or printer, etc. The one or more connection ports can be configured to accept one or more types of cables (e.g., fire wire, USB, serial cable, phone cable, ethernet cable, etc.). In another and/or alternative non-limiting embodiment, when the control unit of the portable monitor is a separate unit from the measuring unit, the control unit of the portable monitor and/or the measuring unit of the portable monitor can include one or more connection ports.

In another and/or additional non-limiting aspect of the present disclosure, the portable monitor includes one or more circuits and/or microprocessors (e.g., Intel® processor, AMD processor, flash memory, hard drive, etc.) to operate one or more software and/or firmware and/or hardware programs (e.g., calibration hardware/software/firmware, flow rate calculation hardware/software/firmware, BTU calculation software and/or firmware, gas analysis hardware/software/firmware, communication hardware/software/firmware, mode of operation hardware/software/firmware, pressure analysis hardware/software/firmware, temperature analysis hardware/software/firmware, etc.) that are loaded/included in the portable monitor. In another and/or alternative non-limiting embodiment, when the control unit of the portable monitor is a separate unit from the measuring unit, the control unit of the portable monitor and/or the measuring unit of the portable monitor can include one or more circuits and/or microprocessors.

In another and/or additional non-limiting aspect of the present disclosure, the portable monitor can optionally include one or more expansion slots (e.g., Type 1 and/or Type II expansion slots) to enable additional hardware and/or software and/or firmware to be added to the portable monitor (added memory, bar code scanner, wireless technology, etc.). In another and/or alternative non-limiting embodiment, when the control unit of the portable monitor is a separate unit from the measuring unit, the control unit of the portable monitor and/or the measuring unit of the portable monitor can include one or more expansion slots.

In another and/or additional non-limiting aspect of the present disclosure, the portable monitor can optionally include one or more sensors to detect/measure ambient conditions (e.g., temperature, pressure, humidity, etc.). In another and/or alternative non-limiting embodiment, when the control unit of the portable monitor is a separate unit from the measuring unit, the control unit of the portable monitor and/or the measuring unit of the portable monitor can include one or more sensors to detect/measure ambient conditions.

In another and/or additional non-limiting aspect of the present disclosure, the portable monitor can optionally include one or more filters, liquid traps, etc., to protect one or more components of the portable monitor when testing fluids (e.g., landfill gas, etc.). In another and/or alternative non-limiting embodiment, when the control unit of the portable monitor is a separate unit from the measuring unit, the measuring unit of the portable monitor can include one or more filters or liquid traps.

In another and/or additional non-limiting aspect of the present disclosure, when the control unit of the portable monitor is a separate unit from the measuring unit, the control unit can optionally be a highly durable portable hand-held device (e.g., mobile phone device, PDA device, Palm PC device, BLACKBERRY® device, augmented reality glasses, virtual reality glasses, etc.).

In another and/or additional non-limiting aspect of the present disclosure, when the control unit of the portable monitor is a separate unit from the measuring unit, the control unit of the portable monitor optionally has a weight and size that are less than the measuring unit of the portable monitor. In one non-limiting aspect of this embodiment, the control unit of the portable monitor has a weight of less than about 5 lbs., typically less than about 2 lbs., and more typically less than about 1.5 lbs. The control unit of the portable monitor typically has a volume of less than about 100 cubic in., typically less than about 75 cubic in., and more typically less than about 50 cubic in.

In another and/or additional non-limiting aspect of the present disclosure, when the control unit of the portable monitor is a separate unit from the measuring unit, the control unit includes one or more circuits and/or microprocessors (e.g., Intel® processor, AMD processor, flash memory, etc.) to operate one or more software and/or firmware and/or hardware programs that are loaded in the control unit. Non-limiting examples of software and/or firmware that can be loaded in the control unit include, but are not limited to, GPS software and/or firmware, navigation software and/or firmware, wireless communication software and/or firmware, photograph/video software and/or firmware, sound/music software and/or firmware, sound recording software and/or firmware, voice recognition software and/or firmware, file/data transfer software and/or firmware, internet browser software and/or firmware, word processor software and/or firmware, touch screen software and/or firmware, database software and/or firmware, spreadsheet software and/or firmware, operating system software and/or firmware, scanner software and/or firmware, printer software and/or firmware, power point software and/or firmware, CAD software and/or firmware, email software and/or firmware, calendar software and/or firmware, address book software and/or firmware, security software and/or firmware, TV software and/or firmware, video software/firmware, radio software and/or firmware, data management software and/or firmware, software and/or firmware to operate/monitor the portable monitor of the portable monitor, calibration software and/or firmware for the portable monitor, handwriting recognition software and/or firmware, diagnostic software and/or firmware for the portable monitor, time/date/timer software and/or firmware, software and/or firmware to make recommendations for landfill gas flow rate into well, BTU calculation software and/or firmware, LEL calculation software and/or firmware, EPA software and/or firmware, environmental software and/or firmware, software and/or firmware used to process landfill well or testing location data, software and/or firmware to process gas data, software and/or firmware to process liquid data, software and/or firmware to process flow rates, software and/or firmware to process temperature determinations, temperature control software and/or firmware, GPS software and/or firmware, file management software and/or firmware, office-type software and/or firmware, communication software and/or firmware, calibration software/firmware, etc. As can be appreciated, when the portable monitor is a single unit, such software and/or firmware can be included in the single unit of the portable monitor.

In another and/or additional non-limiting aspect of the present disclosure, when the control unit of the portable monitor is a separate unit from the measuring unit, the control unit can optionally include a camera, microphone, speaker, etc., to enhance the multimedia features of the control unit; however, this is not required. The control unit optionally can be used with or be incorporated into VR glasses (virtual reality glasses) and AR glasses (augmented reality glasses).

In another and/or additional non-limiting aspect of the present disclosure, when the control unit of the portable monitor is a separate unit from the measuring unit, the control unit can optionally include one or more indicators to facilitate in the use and/or operation of the control unit. Such indicators can include, but are not limited to, battery level indicator, battery charge indicator, battery use indicator, on/off indicator, coupler indicator to indicate when coupler is properly and/or improperly connected, coupler indicator to indicate when coupler is in use, malfunction indicator, etc.

The one or more indicators can be in a variety of forms such as, but not limited to, a sound indicator, a visual indicator (LED light, LCD light or panel, incandescent light, etc.).

In another and/or additional non-limiting aspect of the present disclosure, when the portable monitor optionally includes a control unit and a measuring unit, the control unit of the portable monitor can optionally include one or more monitors/displays (e.g., LCD panel, etc.) to enable an operator to view/use one or more operations and/or functions of the control unit of the portable monitor, view one or more indicators for the control unit of the portable monitor, view/control one or more features of the measuring unit of the portable monitor, view/use one or more software and/or firmware programs on the control unit of the portable monitor, and/or view/use email and/or text messages, etc.

In another and/or additional non-limiting aspect of the present disclosure, when the portable monitor optionally includes a control unit and a measuring unit, the control unit of the portable monitor optionally includes one or more buttons and/or switches. The one or more buttons and/or switches can be used to enable an operator to activate and/or deactivate one or more functions of the control unit of the portable monitor and/or measuring unit of the portable monitor, to display and/or access information from the control unit of the portable monitor and/or measuring unit of the portable monitor, to provide instructions and/or information to the control unit of the portable monitor and/or measuring unit of the portable monitor, volume control, display brightness control, etc.

In another and/or additional non-limiting aspect of the present disclosure, the portable monitor of the present disclosure can optionally include one or more heating elements. The one or more heating elements (when used) provide heating to one or more internal and/or external components of the portable monitor. One or more components of prior art portable monitors can be prone to sluggishness and even failure when the portable monitor is used in a cold environment (i.e., temperature of less than about 30-40° F.). The portable monitor of the present disclosure overcomes this problem by the optional use of one or more heating elements. In one non-limiting embodiment of the disclosure, the one or more heating elements are configured to at least periodically maintain the temperature of one or more components of the portable monitor above about 10° F., typically above about 20° F., more typically about 30° F., even more typically above about 40° F., and still even more typically above about 50° F. The one or more heating elements can be positioned on and/or in the portable monitor to a) maintain all of the components at least periodically above a certain temperature, or b) only maintain one or more components of the portable monitor and/or one or more regions of the portable monitor at least periodically above a certain temperature. In another and/or additional non-limiting embodiment of the disclosure, the one or more heating elements are located at least partially internally of the housing of the portable monitor. In this particular non-limiting embodiment, the one or more heating elements are partially or fully integrated in the housing of the portable monitor. As can be appreciated, the one or more heating elements can be detachably secured in the housing of the portable monitor. For example, the housing can include one or more accessible cavities that allows for the insertion and/or removal of one or more components of the one or more heating elements from the housing. In still another and/or additional non-limiting embodiment of the disclosure, the one or more heating elements are at least partially located on the exterior of the housing of the portable monitor. In one non-limiting aspect of this embodiment, one or more heating elements can be removably or irremovably connected to one or more exterior portions of the housing of the portable monitor. In one non-limiting configuration, a heating jacket can be used to at least partially encapsulate one or more portions of the housing of the portable monitor. The heating jacket can be configured to detachably connect to the housing of the portable monitor so the heating jacket can be used only when needed or desired. As can be appreciated, many other or additional configurations of external heating elements can be used to heat one or more portions of the portable monitor. In yet another and/or additional non-limiting embodiment of the disclosure, the one or more heating elements can include an electric heating coil. As can be appreciated, other or additional types of heating elements can be used. (e.g., radiation elements, etc.). In still yet another and/or additional non-limiting embodiment of the disclosure, the one or more heating elements are powered by an internal and/or external power source. In one non-limiting aspect of this embodiment, the portable monitor includes an internal power source (e.g., battery, fuel cell, solar cell, etc.) to at least partially energize the one or more heating elements. As can be appreciated, the internal power source can be used to power one or more other components of the portable monitor; however, this is not required. The internal power source can be a rechargeable and/or replaceable power source. In another and/or additional non-limiting aspect of this embodiment, the portable monitor includes an external power source (e.g., external battery pack, electric plug to plug into a 120V/220V electric plug, etc.) to at least partially energize the one or more heating elements. As can be appreciated, the external power source can be used to power one or more other components of the portable monitor; however, this is not required. As can also be appreciated, the external power source can be used to recharge an internal power source when an internal power source exists in the housing of the portable monitor; however, this is not required. In another and/or additional non-limiting embodiment of the disclosure, the one or more heating elements can be configured to be manually and/or automatically activated. In one non-limiting aspect of this embodiment, the heating elements can be manually activated by a user. Such activation can be by any number of means (e.g., remote activation, switch activation, connection to a power source, etc.). This arrangement allows a user to manually activate one or more of the heating elements when the user determines that the environment is potentially cold enough to possibly adversely affect the portable monitor. In another and/or additional non-limiting aspect of this embodiment, one or more heating elements can be configured to automatically activate when a predetermined low temperature has been detected. The predetermined low temperature setting can be a factory setting and/or a manual setting by an operator. In one non-limiting configuration, one or more temperature sensors (e.g., temperature coil, electronic sensor, etc.) are positioned on and/or in one or more regions of the housing of the portable monitor to monitor a surrounding temperature. As can be appreciated, other or additional arrangements can be used. In this arrangement, the portable monitor causes one or more heating elements to activate when a low threshold temperature has been detected to prevent the temperature of one or more components of the portable monitor to become too cold. In still another and/or additional non-limiting aspect of this embodiment, when an automatic activation arrangement is used, the portable monitor can be configured to allow a user to manually activate and/or deactivate one or more of the heating elements when so desired; however, this is not required. In yet another and/or additional non-limiting aspect of this embodiment, the portable monitor can include a deactivator to automatically deactivate one or more heating elements when the sensed temperature of the heating element and/or the region about the heating element exceeds a predetermined temperature, and/or the one or more heating elements have been activated for a certain period of time; however, this is not required. The predetermined low temperature setting and/or time period of activation setting can be a factory setting and/or a manual setting by an operator. In one non-limiting arrangement, the portable monitor includes a plurality of heating elements or pads. The heating elements or pads are positioned inside the protective housing of the portable monitor. The heating pads are activated and deactivated by a microprocessor. A plurality of thermocouples are located on or near various components inside the housing of the portable monitor. Generally, these thermocouples are located in important or critical positions on one or more components in the housing (e.g., printed circuit boards, gas measuring components, pumps, etc.). The thermocouples are configured to send information to the microprocessor, which then uses such information to activate or deactivate one or more of the heating elements or pads. The thermocouples thus provide feedback information to the microprocessor to enable the microprocessor to properly activate or deactivate a certain heating element or pad. As can be appreciated, the microprocessor can activate/deactivate some or all of the heating elements or pads based on the information received from one or more thermocouples that are positioned in different regions of the housing. In one non-limiting arrangement, the microprocessor activates one or more heating elements or pads when the thermocouple measurement from one or more thermocouples is equal to or below some predefined threshold value and deactivates one or more heating elements or pads when the thermocouple measurement from one or more thermocouples is equal to or above some predefined threshold value. In one non-limiting specific arrangement, all of the heating elements or pads are activated when the lowest reading from one or more thermocouple measurements (e.g., one thermocouple measurement, two different thermocouple measurements, three different thermocouple measurements, four different thermocouple measurements, etc.) are equal to or below a threshold value, and all of the heating elements or pads are deactivated when the highest reading from one or more thermocouple measurements are equal to or above a threshold value. In this specific arrangement, generally less than all of the thermocouples in the housing are generating readings above/below/equal to some upper or lower predetermined value to cause the microprocessor to activate/deactivate all or some subset of the heating elements or pads in the housing. Generally, the predefined low temperature level is no less than about −10° F., generally no less than about −4° F., more typically no less than about 0° F., and still more typically no less than about 10° F. As can be appreciated, the predefined low temperature level can be set at higher temperatures (e.g., 20° F., 32° F., 40° F., etc.). The predefined high temperature level is generally less than about 130° F., typically less than about 122° F., more typically less than about 115° F., and even more typically less than about 110° F.

In another and/or additional non-limiting aspect of the present disclosure, the portable monitor optionally includes one or more cooling elements. The one or more cooling elements (when optionally used) provide cooling to one or more internal and/or external components of the portable monitor. When the temperature of one or more components of the portable monitor becomes too hot, the one or more components can be damaged and/or malfunction. To address this overheating problem, the portable monitor of the present disclosure can include one or more cooling elements. In one non-limiting embodiment of the disclosure, the one or more cooling elements are configured to at least periodically maintain the temperature of one or more components of the portable monitor below about 200° F., typically below about 150° F., more typically below about 120° F., and even more typically below about 100° F. The one or more cooling elements can be positioned on and/or in the portable monitor to a) maintain all of the components at least periodically below a certain temperature, or b) only maintain one or more components of the portable monitor and/or one or more regions of the portable monitor at least periodically below a certain temperature. In another and/or additional non-limiting embodiment of the disclosure, the one or more cooling elements are located at least partially internally of the housing of the portable monitor. In this particular non-limiting embodiment, the one or more cooling elements are partially or fully integrated in the housing of the portable monitor. As can be appreciated, the one or more cooling elements can be detachably secured in the housing of the portable monitor. For example, the housing can include one or more accessible cavities allowing for the insertion and/or removal of one or more components of the one or more cooling elements from the housing. In still another and/or additional non-limiting embodiment of the disclosure, the one or more cooling elements are at least partially located on the exterior of the housing of the portable monitor. In one non-limiting aspect of this embodiment, one or more cooling elements can be removably or irremovably connected to one or more exterior portions of the housing of the portable monitor. In one non-limiting configuration, a cooling jacket could be used that is configured to at least partially encapsulate one or more portions of the housing of the portable monitor. The cooling jacket can be configured to detachably connect to the housing of the portable monitor so the cooling jacket can be used only when needed or desired. As can be appreciated, many other or additional configurations of external cooling elements can be used to cool one or more portions of the portable monitor. In yet another and/or additional non-limiting embodiment of the disclosure, the one or more cooling elements include an electric fan. As can be appreciated, other or additional types of cooling elements can be used (e.g., heat sink arrangement, ice or chemical cooling pouch, etc.). In still yet another and/or additional non-limiting embodiment of the disclosure, the one or more cooling elements are powered by an internal and/or external power source. In one non-limiting aspect of this embodiment, the portable monitor includes an internal power source (e.g., battery, fuel cell, solar cell, etc.) to at least partially energize the one or more cooling elements. As can be appreciated, the internal power source can be used to power one or more other components of the portable monitor; however, this is not required. The internal power source can be a rechargeable and/or replaceable power source. In another and/or additional non-limiting aspect of this embodiment, the portable monitor includes an external power source (e.g., external battery pack, electric plug to plug into a 120V/220V electric plug, etc.) to at least partially energize the one or more cooling elements. As can be appreciated, the external power source can be used to power one or more other components of the portable monitor; however, this is not required. As can also be appreciated, the external power source can be used to recharge an internal power source when an internal power source exists in the housing of the portable monitor; however, this is not required. In another and/or additional non-limiting embodiment of the disclosure, the one or more cooling elements can be configured to be manually and/or automatically activated. In one non-limiting aspect of this embodiment, the cooling elements can be manually activated by a user. Such activation can be by any number of means (e.g., remote activation, switch activation, connection to a power source, etc.). This arrangement allows a user to manually activate one or more of the cooling elements when the user determines that the environment is potentially hot enough to possibly adversely affect the portable monitor. In another and/or additional non-limiting aspect of this embodiment, one or more cooling elements can be configured to automatically activate when a predetermined high temperature has been detected. The predetermined high temperature setting can be a factory setting and/or a manual setting by an operator. In one non-limiting configuration, one or more temperature sensors (e.g., temperature coil, electronic sensor, etc.) are positioned on and/or in one or more regions of the housing of the portable monitor to monitor a surrounding temperature. As can be appreciated, other or additional arrangements can be used. In this arrangement, the portable monitor causes one or more cooling elements to activate to prevent the temperature of one or more components of the portable monitor from becoming too hot. In still another and/or additional non-limiting aspect of this embodiment, when an automatic activation arrangement is used, the portable monitor can be configured to allow a user to manually activate and/or deactivate one or more of the cooling elements when so desired; however, this is not required. In yet another and/or additional non-limiting aspect of this embodiment, the portable monitor can include a deactivator to automatically deactivate one or more cooling elements when the sensed temperature of the cooling element and/or region about the cooling element falls below a predetermined temperature, and/or the one or more cooling elements have been activated for a certain period of time; however, this is not required. The predetermined temperature setting and/or time period of activation setting can be a factory setting and/or a manual setting by an operator.

In another and/or additional non-limiting aspect of the present disclosure, the portable monitor is optionally configured to measure $H_2$ at ETLF facilities and biogas locations. The portable monitor is configured to enable users to measure both low and high levels of $H_2$ in the presence of typical landfill gas constituents and gases at typical biogas facilities. For landfills, the ability to accurately determine $H_2$ levels in a gas sample is a potentially valuable tool to monitor the status of the fermentation process and methanogenesis reactions at ETLF facilities. The detection of $H_2$ levels in landfill gas can be an early indicator of the status of reactions taking place in a landfill. Early detection of the status of the fermentation process and methanogenesis reactions at ETLF facilities and being able to trend $H_2$ concentrations in the landfill gas over time will help determine the movement and status of the reactions in the landfill. This proactive measure will allow the landfill owner to plan and upgrade infrastructure as well as to potentially manage the reactions in the landfill.

In another and/or additional non-limiting aspect of the present disclosure, the portable monitor is optionally configured to use a multipath fluid flow system through the portable monitor to protect certain types of sensors from damage, contamination, or producing unreliable readings for certain components in a fluid sample. Chemical sensors/analyzers for components such a carbon monoxide and hydrogen sulfide are susceptible to being contaminated by hydrogen. Hydrogen levels that exceed 1-2 vol. % in a fluid sample can contaminate the chemical sensors/analyzers for carbon monoxide and hydrogen sulfide, thereby making such chemical sensors/analyzers inoperable, unusable, and/or result in false/inaccurate readings. The portable monitor in accordance with the present disclosure uses an arrangement that isolates chemical sensors/analyzers for carbon monoxide and/or hydrogen sulfide from the sampled fluid stream until the hydrogen content of the sampled fluid stream can be determined. If the hydrogen content in the sampled stream is determined to be lower than a certain amount, the portable monitor can then optionally direct at least a portion of the sampled fluid stream to the chemical sensors/analyzers for carbon monoxide and/or hydrogen sulfide so that such chemical sensors/analyzers can then accurately measure the content of carbon monoxide and/or hydrogen sulfide in the sampled fluid stream without damaging and/or contaminating the chemical sensors/analyzers for carbon monoxide and/or hydrogen sulfide. However, if the hydrogen level of the sampled fluid stream is found to be too high, the portable monitor will keep the chemical sensors/analyzers for carbon monoxide and/or hydrogen sulfide isolated from the sampled fluid stream to not damage and/or contaminate the chemical sensors/analyzers for carbon monoxide and/or hydrogen sulfide. The isolation of the chemical sensors/analyzers for carbon monoxide and/or hydrogen sulfide can be accomplished by one or more manual valves (e.g., manually openable and closeable valve, ball valves, butterfly valves, globe valves, gate valves, diaphragm valves, etc.) or controlled valves (e.g., solenoid valve, motorized valve, hydraulic valve, linear motion valve, rotary motion valve, etc.). In one non-limiting embodiment, when the portable monitor includes a control unit and a measuring unit, the multipath fluid flow system (when used) exists only in the measuring unit.

In another and/or additional non-limiting aspect of the present disclosure, the portable monitor is optionally configured to use a valve (e.g., solenoid valve or other controllable valve, manual valve, etc.) to protect chemical sensors/analyzers from damage by $H_2$. The portable monitor initially directs sampled fluid along Sample Path 1 to one or more chemical sensors/analyzers (e.g., electrochemical cell, infrared cell, TDL (laser) and UV absorption spectroscopy, thermal-conductivity detection, etc.) to measure the concentration of $H_2$ and optionally one or more of $CH_4$, $CO_2$, $O_2$ in the sampled fluid.

In another and/or additional non-limiting aspect of the present disclosure, the concentration of $H_2$ can optionally be determined by a $H_2$ sensor. In one non-limiting arrangement, the concentration of $H_2$ is determined by both a $H_2$ sensor and a $CH_4$ sensor. It has been found that concentration of $H_2$ as determined by a $H_2$ sensor can provide a false reading when there are elevated levels of $CH_4$ in the sampled fluid. As such, $CH_4$ value compensation calculations can optionally be used to adjust the measured levels of $H_2$ as determined by a $H_2$ sensor in view of the measure concentration of $CH_4$ to calculate a corrected $H_2$ concentration value for the sampled fluid. The portable monitor can optionally include $H_2/CH_4$ concentration correction tables, correction curves, and/or equations to provide a corrected $H_2$ concentration value based on the measured $H_2$ and $CH_4$ in the sampled fluid.

In another and/or additional non-limiting aspect of the present disclosure, the portable monitor includes a valve system that defaults to initially directing sampled fluid to Sample Path 1. Such a valve system could include the use of one or more manual valves and/or solenoid valves; however, other or additional types of valves can be used. If the concentration of $H_2$ is determined to be too high (e.g., above 0.1 vol. %, above 1 vol. %, above 2 vol. %, above 0.01-4 vol. % and all values and ranges therebetween), the sampled fluid remains in Sample Path 1 and 1) all or a portion of the sampled fluid is expelled from the portable monitor, and/or 2) at least a portion of the sampled fluid is saved in a sampling container for later testing for other gas components in the sampled fluid (e.g., hydrogen sulfide, carbon monoxide, etc.). If the concentration of $H_2$ is determined to be low or acceptable (i.e., below the too high level), at least a portion of the sampled fluid can be directed to Sample Path 2. As can be appreciated, when the sampled fluid is allowed to flow to Sample Path 2, the sampled fluid can a) to fully diverted to Sample Path 2 thereby eliminating further flow through Sample Path 1, or b) be allowed to flow through both Sample Path 1 and 2. When the sampled fluid is allowed to simultaneously flow through both Sample Paths 1 and 2, the chemical sensors/analyzers in both Sample Paths 1 and 2 can optionally simultaneously measure/detect/analyze the components of the sampled fluid. Sample Path 2 can include sensors such as a carbon monoxide sensor, a hydrogen sulfide sensor, and/or one or more other or additional sensors. Generally, one or more sensor used in Sample Path 2 could provide false readings and/or can be damaged when there is a too high concentration of $H_2$ in the sampled fluid; however, this is not required. If automatic valves are used to determine the flow path of the fluid based on the $H_2$ content in the fluid, a preset or predefined maximum level can be manually or automatically set to cause the flow path to be automatically selected based on the measured $H_2$ content in the fluid; however, this is not required.

In another and/or additional non-limiting aspect of the present disclosure, the concentration of Balance Gas Value of the sampled fluid streamed is optionally determined by first determining the concentration of one or more components in the fluid stream; however, this is not required. The portable monitor optionally includes a valve system that defaults to initially directing sampled fluid to Sample Path 1. Such a valve system could include the use of one or more manual valves and/or solenoid valves; however, other or additional types of valves can be used. If the Balanced Gas Value is determined to be too high (e.g., above 0.1 vol. %, above 1 vol. %, above 2 vol. %, above 0.01-4 vol. % and all values and ranges therebetween), the portable monitor could be optionally configured to maintain the sampled fluid remains in Sample Path 1 and then 1) all or a portion of the sampled fluid is expelled from the portable monitor, and/or 2) at least a portion of the sampled fluid is saved in a sampling container for later testing for other gas components in the sampled fluid (e.g., hydrogen sulfide, carbon monoxide, etc.). If the Balanced Gas Value is determined to be low or acceptable (i.e., below the too high level), then the portable monitor could be optionally configured to allow at least a portion of the sampled fluid to be directed to Sample Path 2. Sample Path 2 can include sensors such as a carbon monoxide sensor, a hydrogen sulfide sensor and/or one or more other or additional sensors. Generally, one or more sensor in Sample Path 2 could provide false readings and/or can be damaged when there is a too high concentration of $H_2$ in the sampled fluid; however, this is not required. In one non-limiting embodiment, the Balanced Gas Value is equal to 100% minus the determined values of one or more of % $CH_4$, % $CO_2$, % $O_2$, and % $H_2$. As can be appreciated, other or additional components can be added to the Balanced Gas Value determination. In one non-limiting example, the Balanced Gas Value is equal to 100% minus the combined determined values of % $CH_4$, % $CO_2$, % $O_2$, and % $H_2$. In one specific arrangement, when the Balanced Gas Value is 0.1-4 and all values and ranges therebetween (e.g., 1, 2, etc.), the portable monitor will either automatically open a valve or signal and/or allow the user to open a valve to allow the sampled fluid to flow into Sample Path 2. This control of sampled fluid into Sample Path 2 will facilitate in preventing the CO and/or $H_2S$ analyzer cells in Sample Path 2 from being damaged and/or providing false elevated values due to the cross sensitivity of high $H_2$ in the sampled fluid. As can be appreciated, the control of fluid to Sample Paths 1 and 2 could also or alternatively be determined by the hydrogen content of the fluid when measured in Path 1. If the measured hydrogen level is at or above a certain value, the fluid is not allowed to flow into Sample Path 2. If the measured hydrogen level is at or below a certain value, the fluid is allowed to flow into Sample Path 2.

In another and/or additional non-limiting aspect of the present disclosure, the portable monitor optionally includes an exhaust path for both of Sample Paths 1 and 2, or may optionally include a single exhaust path for Sample Paths 1 and 2 wherein a valve system (e.g., manual and/or automatic valve system) is used to combine the exhaust paths of Sample Paths 1 and 2 to a single exhaust path that exists the portable monitor. As can be appreciated, Sample Paths 1 and 2 can be two distinct and separate fluid paths for the sampled fluid, or can be a single sample path wherein different chemical analyzers are controllability isolated from the single path and/or controllably activated and deactivated in the single path. As can be appreciated, many arrangements that fall within the scope of the disclosure can be used to control the exposure of certain chemical analyzers to a sampled fluid at one time period to initially determine one or more components of the sampled fluid and then make a determination if the sampled fluid should be analyzed or not analyzed by one or more other chemical analyzed based on an earlier determination of the one or more components in the sampled fluid.

In another and/or additional non-limiting aspect of the present disclosure, the portable monitor optionally includes Sample Paths 1 and 2 wherein a valve system first directs sampled fluid to Sample Path 1 wherein at least the hydrogen content of the sampled fluid is determined. Thereafter, if the hydrogen content and/or the Balanced Gas Value of the sampled fluid is below a certain level, the sampled fluid is then directed to Sample Path 2 wherein one or more components of the sampled fluid is detected. In one non-limiting embodiment, Sample Path 2 includes one or more chemical analyzers (e.g., carbon monoxide analyzer, hydrosulfide analyzer, hydrogen analyzer, etc.). Generally, Sample Path 2 includes one or more different chemical analyzers from the chemical analyzers used in Sample Path 1.

In another and/or additional non-limiting aspect of the present disclosure, the portable monitor optionally includes Sample Paths 1 and 2 wherein Sample Path 2 includes a chemical analyzer for hydrogen sulfide and a separate chemical analyzer for carbon monoxide. In one non-limiting embodiment, the chemical analyzer for hydrogen sulfide is upstream to the chemical analyzer for carbon monoxide such that the sampled fluid in Sample Path 2 is analyzed for hydrogen sulfide prior to being analyzed for carbon monoxide; however, this is not required.

In another and/or additional non-limiting aspect of the present disclosure, the portable monitor optionally includes Sample Paths 1 and 2 wherein Sample Path 2 includes a chemical analyzer for hydrogen sulfide and one or more separate chemical analyzers for carbon monoxide and/or hydrogen. In one non-limiting embodiment, the chemical analyzer for hydrogen sulfide is upstream to the chemical analyzer for carbon monoxide such that the sampled fluid in Sample Path 2 is analyzed for hydrogen sulfide prior to being analyzed for carbon monoxide; however, this is not required. In one non-limiting embodiment, the chemical analyzer for hydrogen sulfide is upstream to the chemical analyzer for carbon monoxide and hydrogen such that the sampled fluid in Sample Path 2 is analyzed for hydrogen sulfide prior to being analyzed for carbon monoxide and hydrogen; however, this is not required. After the hydrogen sulfide content is measured, a) the content of carbon monoxide in the stream in Sample Path 2 can be measured prior to the content measurement of hydrogen in Sample Path 2, b) the content of hydrogen and carbon monoxide in the stream in Sample Path 2 can be simultaneously measured in Sample Path 2. In one non-limiting embodiment, the portable monitor optionally uses the detected amount and/or calculated amount of hydrogen in the sampled fluid to adjust the amount of carbon monoxide in the sampled fluid that was determined by the carbon monoxide chemical analyzer. It has been found that low levels of hydrogen in the sampled fluid can affect the amount of CO measured by the carbon monoxide chemical analyzer. The portable monitor can optionally include hydrogen/CO concentration correction tables, correction curves, and/or equations used to provide a corrected CO concentration value based on the measured $H_2$ and/or $CH_4$ in the sampled fluid. The measured $H_2$ used to correct the measured CO concentration in the sampled fluid can be from the $H_2$ analyzer/sensor in Sample Path 1, in Sample Path 2, or from both Sample Paths 1 and 2. When Sample Path 2 is used, the hydrogen content of the sampled fluid is typically at a low concentration (e.g., less than 0.5-2 vol. % and all values and ranges therebetween, less than 2 vol. %, less than 1 vol. %, etc.). The portable monitor can include software and/or firmware to adjust the CO content in the sampled fluid based on the low levels of hydrogen in the sampled fluid. Also or alternatively, some CO sensors have software/firmware/hardware cells that can include $H_2$ compensation so that measured levels of CO are adjusted by the amount of hydrogen in the measured fluid. When such a CO sensor is used, the use of a low-level hydrogen sensor could optionally be eliminated from Sample Path 2; however, this is not required. Also, a low-level hydrogen sensor can be eliminated in Sample Path 2 if the corrected CO concentration value is based on the measured $H_2$ and/or $CH_4$ in the sampled fluid from Sample Path 1.

In another and/or additional non-limiting aspect of the present disclosure, the portable monitor optionally includes Sample Paths 1 and 2 wherein Sample Path 2 includes a chemical analyzer for hydrogen sulfide and one or more separate chemical analyzers for carbon monoxide and/or hydrogen, and wherein one or more fluid filters are optionally positioned between the chemical analyzer for hydrogen sulfide and the one or more chemical analyzers for carbon monoxide and/or hydrogen to partially or fully remove one or more components in the sampled fluid prior to being analyzed by the one or more chemical analyzers for carbon monoxide and/or hydrogen; however, this is not required. The one or more fluid filters (when used) can optionally be configured to partially or fully remove one or more components from the sampled fluid selected from hydrogen, oxygen, nitrogen, methane, hydrogen, and/or hydrogen sulfide. In one non-limiting embodiment, the one or more fluid filters are configured to partially or fully remove at least hydrogen sulfide from the fluid stream prior to the sampled fluid being analyzed by the one or more chemical analyzers for carbon monoxide and/or hydrogen. Such a fluid filter (when used) provides additional protection for the carbon monoxide chemical analyzer and/or the hydrogen chemical analyzer that can be adversely impacted (e.g., contaminated, damaged, etc.) by hydrogen sulfide in the sampled fluid. The one or more fluid filters can be removable and/or replaceable in the portable monitor; however, this is not required. In one non-limiting arrangement, Sample Path 2 includes a hydrogen sulfide chemical analyzer located upstream from a carbon monoxide chemical analyzer and wherein one or more fluid filters are located between the hydrogen sulfide chemical analyzer and the carbon monoxide chemical analyzer such that the one or more fluid filters partially or fully remove hydrogen sulfide from the sampled fluid prior to the sampled fluid being analyzed by the carbon monoxide chemical analyzer. In one non-limiting arrangement, Sample Path 2 includes a hydrogen sulfide chemical analyzer located upstream from a hydrogen chemical analyzer and wherein one or more fluid filters are located between the hydrogen sulfide chemical analyzer and the hydrogen chemical analyzer such that the one or more fluid filters partially or fully remove hydrogen sulfide from the sampled fluid prior to the sampled fluid being analyzed by the hydrogen chemical analyzer. In one non-limiting arrangement, Sample Path 2 includes a hydrogen sulfide chemical analyzer that is located upstream from a carbon monoxide chemical analyzer and a hydrogen chemical analyzer and wherein one or more fluid filters are located between the hydrogen sulfide chemical analyzer and the carbon monoxide chemical and hydrogen analyzers such that the one or more fluid filters partially or fully remove hydrogen sulfide from the sampled fluid prior to the sampled fluid being analyzed by the carbon monoxide and hydrogen chemical analyzers. In another non-limiting embodiment, when the hydrogen chemical analyzer is sensitive to the content of hydrogen sulfide in the sampled fluid, the hydrogen chemical analyzer can be located after or downstream from the one or more fluid filters configured to partially or fully remove hydrogen sulfide from the sampled fluid. However, if the hydrogen chemical analyzer is not sensitive to the content of hydrogen sulfide in the sampled fluid, the location of the hydrogen chemical analyzer in the portable monitor is not limited to any particular location.

In another and/or additional non-limiting aspect of the present disclosure, the portable monitor optionally includes a filter status indicator to detect and/or determine and/or display and/or transmit information regarding the status of the one or more fluid filters (when used). In one non-limiting embodiment, the one or more fluid filters can contain color-changing media as an indicator to the user that the filter media is partially or fully spent. The portable monitor can optionally also or alternatively utilize a process that electronically and or optically identifies that the color changing media contained in the one or more fluid filters is partially or fully spent. The portable monitor can optionally use software or firmware to observe the output of the optical, capacitive, resistive, inductive, or other sensor technology which measures the physical change which has occurred in the one or more fluid filters and/or status indicator for the one or more fluid filters, and then optionally recommend that the user change the one or more fluid filters. The optional software or firmware used to monitor the status of one or more of the fluid filters can optionally include adjustable, fixed, or variable criteria which can be used to examine a) the chemical analyzer readings from the time the one or filters were first used, b) number of times chemical analyzers were used since the one or more fluid filters were first used, c) fluid composition of sampled fluids tested since the one or more fluid filters were first used, d) cumulative fluid composition of sampled fluids tested since the one or more fluid filters were first used, e) the use and/or status monitor on the one or more fluid filters, f) the time period since filters were first used, and/or g) the number of times portable monitor was used since the one or more fluid filters was first used. The portable monitor can optionally include a filter reset storage EEPROM or non-volatile memory to record state or status of the one or more fluid filters, and can optionally be reset when the one or more fluid filters are replaced. In another non-limiting embodiment, the one or more fluid filters can optionally use one or more fluid filters that have an internal memory to allow reading of proper filter type from a filter internal memory such as an EEPROM, FRAM, RFID, or near field other identification tag, and/or include a color-changing material that enables a user to visually see status of the filter and whether it needs to be changed.

In another and/or additional non-limiting aspect of the present disclosure, the portable monitor optionally includes a system that checks whether 1) proper chemical analyzers are used, 2) chemical analyzers are located in proper locations in the portable monitor and/or properly connected in the proper locations in the portable monitor, 3) any of the chemical analyzers need to be replaced (e.g., expired, contaminated, damaged, etc.), 4) proper fluid filters are positioned in the potable monitor, and/or 5) any of the fluid filters need to be replaced (e.g., expired, used up, damaged, etc.), and the portable monitor can be optionally configured to prevent further operation until one or more of these checked criteria are satisfactory addressed. As can be appreciated, the portable monitor can include other or additional checks to determine the proper functionality of the portable monitor. As can be appreciated, the portable monitor can optionally include a manual override and/or reset to cause the portable monitor to operate even when one or more the status checks is not satisfied.

In another and/or additional non-limiting aspect of the present disclosure, the portable monitor optionally includes a pressure sensor to adjust sensor readings that are affected by changes in pressure in the manifold as well as barometric pressures.

In another and/or additional non-limiting aspect of the present disclosure, the portable monitor optionally includes a temperature sensor to adjust sensor readings that are affected by changes in temperature. In one non-limiting embodiment, the one or more temperature sensors are located on or closely adjacent (e.g., 0.0001-2 inches and any value or ranges therebetween, 0.001-1 inches, 0.001-0.5 inches) to one or more chemical analyzers.

In another and/or additional non-limiting aspect of the present disclosure, the portable monitor optionally allows a user to lock and store the analyzed reading of the sampled fluid once all of the readings are stabilized from the chemical analyzer cells.

In another and/or additional non-limiting aspect of the present disclosure, the portable monitor can optionally include an anti-static material (e.g., polymer coating, paint, etc.) to reduce the potential of damage to the one or more components of the portable monitor, and/or to reduce the potential of igniting the sampled gas which could result in fire and/or an explosion in the portable monitor. In one non-limiting embodiment, the portable monitor can optionally include a low inductance pump, limits on capacitor size, conductive plastic housings, and anti-static paint to reduce the potential or damage to the one or more components of the portable monitor from a static charge and/or other type of electrical discharge, and/or to reduce the potential of igniting the sampled gas from a static charge and/or other type of electrical discharge.

It is a non-limiting object of the present disclosure to provide a portable monitor that can be used to more easily obtain information about fluids.

It is another and/or additional non-limiting object of the present disclosure to provide a portable monitor that can be used to measure fluid pressure and/or fluid composition.

It is another and/or additional non-limiting object of the present disclosure to provide a portable monitor that can be used to measure gas pressures and composition of gases.

It is another and/or additional non-limiting object of the present disclosure to provide a portable monitor that can used to measuring gas pressures and composition of gases from landfills or other testing location (e.g., biogas locations, etc.).

It is another and/or additional non-limiting object of the present disclosure to provide a portable monitor that can measure $H_2$ at ETLF facilities and biogas locations.

It is another and/or additional non-limiting object of the present disclosure to provide a portable monitor that can measure both low and high levels of $H_2$ in the presence of typical landfill gas constituents and gases at typical biogas facilities.

It is another and/or additional non-limiting object of the present disclosure to provide a portable monitor that is optionally configured to use a multipath fluid flow system through the portable monitor to protect certain types of sensors from damage, contamination, or producing unreliable readings for certain components in a fluid sample.

It is another and/or additional non-limiting object of the present disclosure to provide a portable monitor that is optionally configured to use a valve arrangement to protect chemical sensors/analyzers from damage.

It is another and/or additional non-limiting object of the present disclosure to provide a portable monitor that can optionally include compensation calculations to adjust the measured levels of one or more components of the sampled fluid.

It is another and/or additional non-limiting object of the present disclosure to provide a portable monitor that optionally includes one or more fluid filters to partially or fully remove one or more components in the sampled fluid prior to being analyzed by the one or more chemical analyzers.

It is another and/or additional non-limiting object of the present disclosure to provide a portable monitor that optionally includes a filter status indicator to detect and/or determine and/or display and/or transmit information regarding the status of the one or more fluid filters (when used).

It is another and/or additional non-limiting object of the present disclosure to provide a portable monitor that optionally includes a system that checks whether 1) proper chemical analyzers are used, 2) chemical analyzers are located in proper locations in the portable monitor and/or properly connected in the proper locations in the portable monitor, 3) any of the chemical analyzers need to be replaced (e.g., expired, contaminated, damaged, etc.), 4) proper fluid filters are positioned in the portable monitor, and/or 5) any of the fluid filters need to be replaced (e.g., expired, used up, damaged, etc.). The portable monitor can be optionally configured to prevent further operation until one or more of these checked criteria are satisfactory addressed.

It is another and/or additional non-limiting object of the present disclosure to provide a portable monitor that optionally includes a pressure sensor to adjust sensor readings that are affected by changes in pressure in the manifold as well as barometric pressures.

It is another and/or additional non-limiting object of the present disclosure to provide a portable monitor that optionally includes a temperature sensor to adjust sensor readings that are affected by changes in temperature.

It is another and/or additional non-limiting object of the present disclosure to provide a portable monitor that can operate in cold temperatures.

It is another and/or additional non-limiting object of the present disclosure to provide a portable monitor that includes a heater.

It is another and/or additional non-limiting object of the present disclosure to provide a portable monitor that can simultaneously measure three or more pressures.

It is another and/or additional non-limiting object of the present disclosure to provide a portable monitor that includes a control unit and a measuring unit.

It is another and/or additional non-limiting object of the present disclosure to provide a portable monitor that includes wireless communication between a control unit and a measuring unit.

It is another and/or additional non-limiting object of the present disclosure to provide a portable monitor that provides GPS information.

It is another and/or additional non-limiting object of the present disclosure to provide a portable monitor that is configured to obtain and/or measure a plurality of properties of fluid at a test site. The handheld portable monitor is configured to enable the user to easily and conveniently carry the handheld portable monitor to the test site and to enable the user to monitor fluid at the test site and thereafter to enable the user to remove the handheld portable monitor from the test site and thereafter to enable the user to position the handheld portable monitor at another test site to be tested. The handheld portable monitor has a total weight of less than 20 pounds and a total volume of less than 500 cubic inches. The handheld portable monitor includes one or more fluid connectors that enable the handheld portable monitor to test fluid at the test site and thereafter enable the handheld portable monitor to be removed from the tested test site after completion of testing and then later positioned at another test site to be tested. The handheld portable monitor includes a sensor arrangement to obtain and/or to measure properties of the fluid located at the tested test site, the sensor arrangement including at least one pressure sensor and at least one chemical analyzer, the properties of the fluid at the tested test site to be obtained and/or measured including two or more properties selected from the group consisting of a) test site pressure, b) test site temperature, c) LEL, d) UEL, e) test site fluid composition, and f) fluid composition ratio. The handheld portable monitor includes a circuit and/or a processor that processes information to display, store, measure, and/or calculate the two or more properties. The sensor arrangement in the handheld portable monitor is configured to receive information and process such information and to generate one or more types of information selected from the group consisting of i) LEL of the fluid, ii) UEL of the fluid, iii) concentration ratio of methane to carbon dioxide, iv) concentration ratio of balance gas to oxygen, v) concentration of methane, and vi) concentration of hydrogen sulfide. The handheld portable monitor includes storage memory to store information about the tested test site, the location of the tested test site, and the two or more properties that are associated with the tested test site.

It is another and/or additional non-limiting object of the present disclosure to provide a portable monitor including an internal power source, the internal power source configured to power components in the handheld portable monitor.

It is another and/or additional non-limiting object of the present disclosure to provide a portable monitor wherein the sensor arrangement in the handheld portable monitor includes a controller arrangement, a plurality of pressure sensors and a plurality of chemical analyzers, one or more of the pressure sensors is configured to measure a different pressure. The controller arrangement controls each of the pressure sensors to enable the handheld portable monitor to simultaneously measure at least three different fluid pressures from the tested test site. Each of the chemical analyzers is configured to measure a concentration of one or more components in the fluid from the tested test site. One or more of the plurality of the chemical analyzers is configured to measure a concentration of methane, carbon dioxide, and oxygen in the fluid from the tested test site. The fluid pressures includes an applied vacuum on the tested test site, a differential vacuum on the tested test site, and an available vacuum.

It is another and/or additional non-limiting object of the present disclosure to provide a portable monitor wherein the handheld portable monitor includes a display screen and a plurality of buttons positioned under the display screen.

It is another and/or additional non-limiting object of the present disclosure to provide a portable monitor further including a heating system to heat at least one component of the sensor arrangement. The heating system includes a controller arrangement, a thermocouple, and a heating element. The controller arrangement activates the heating element when the controller arrangement obtains information from the thermocouple that a temperature detected by the thermocouple is at or below a predefined low level temperature.

It is another and/or additional non-limiting object of the present disclosure to provide a portable monitor wherein the heating system includes at least three of the thermocouples. The controller arrangement activates the heating element when the controller arrangement obtains information from a majority of the thermocouples that a temperature detected by the majority of the thermocouples is at or below a predefined low level temperature.

It is another and/or additional non-limiting object of the present disclosure to provide a portable monitor wherein the handheld portable monitor includes a handheld portable control unit and a handheld portable measuring unit, each of the handheld portable control unit and the handheld portable measuring unit are contained in separate housings. The handheld portable control unit is configured to monitor and control one or more functions of the handheld portable measuring unit. The handheld portable measuring unit is configured to be removably positioned at the tested test site and be physically removed from the test site after completion of the testing of the test site and subsequently physically positioned at another test site to be tested. The housing of the handheld portable measuring unit at least partially contains the sensor arrangement, the housing of the handheld portable measuring unit including the one or more fluid connectors. The handheld portable control unit is a tablet PC, palm PC, PDA, or smartphone device and is configured to not be required to be physically positioned at the test site that is being tested while the handheld portable measuring unit is removably positioned at the test site during testing of the test site. The handheld portable control unit is absent the one or more fluid connectors. The handheld portable measuring unit has a weight of less than 10 pounds and a volume of less than 300 cubic inches. The handheld portable control unit has a weight of less than 5 pounds and a volume of less than 100 cubic inches.

It is another and/or additional non-limiting object of the present disclosure to provide a portable monitor wherein the plurality of properties of fluid that are obtained and/or measured at a test site include two or more properties selected from the group consisting of a) pressure of the fluid at the test site, b) temperature of the fluid at the test site, c) LEL of the fluid at the test site, d) UEL of the fluid at the test site, e) composition of the fluid at the test site, and f) composition ratio or two of more components in the fluid at the test site.

It is another and/or additional non-limiting object of the present disclosure to provide a portable monitor that is configured to obtain and/or measure one or more properties of fluid at a test site is configured to enable a user to easily and conveniently carry the handheld portable monitor to the site to be tested, and to enable the user to monitor and/or obtain information about one of more properties of the fluid at the test site, and thereafter to enable the user to remove the handheld portable monitor from the test site. The handheld portable monitor has a total weight of less than 20 pounds and a total volume of less than 500 cubic inches. The handheld portable monitor includes one or more fluid connectors that enable the handheld portable monitor to test fluid at the test site and thereafter enable the handheld portable monitor to be removed from the tested test site after completion of testing. The handheld portable monitor includes a sensor system to obtain and/or measure one or more properties of the fluid located at the tested test site, said sensor system including a) first and second sample paths and b) a valve system that controls fluid flow between the first and second sample paths. The first sensor arrangement is connected to the first sample path and the second sensor arrangement is connected to the second sample path. The first sensor arrangement includes a first hydrogen sensor. The valve system includes a path valve wherein the valve system causes the valve to only allow the test fluid to flow through the first sample path when a hydrogen content in the test fluid is at least partially determined by the first hydrogen sensor to be at or above a predetermined level. The valve system causes the path valve to allow the test fluid to flow through the second sample path when the hydrogen content in the test fluid is at least partially determined by the first hydrogen sensor to be below the predetermined level.

It is another and/or additional non-limiting object of the present disclosure to provide a portable monitor wherein the second sensor arrangement includes one or more sensors selected from the group consisting of a second hydrogen sensor, a $H_2S$ sensor and a CO sensor.

It is another and/or additional non-limiting object of the present disclosure to provide a portable monitor wherein the first sensor arrangement further includes one or more sensors selected from the group consisting of a $CH_4$ sensor, an oxygen sensor, and a $CO_2$ sensor.

It is another and/or additional non-limiting object of the present disclosure to provide a portable monitor wherein the second sensor arrangement includes the second hydrogen sensor, said second hydrogen sensor is configured to detect lower levels of hydrogen in the test fluid than the first hydrogen sensor in the first sensor arrangement.

It is another and/or additional non-limiting object of the present disclosure to provide a portable monitor wherein the second sensor arrangement includes the $H_2S$ sensor and a $H_2S$ filter wherein the $H_2S$ sensor is positioned upstream from the second hydrogen sensor and the $H_2S$ filter is configured to at least partially remove $H_2S$ from the test fluid as the test fluid passes through the $H_2S$ filter. The $H_2S$ filter position between the $H_2S$ sensor and the second hydrogen sensor.

It is another and/or additional non-limiting object of the present disclosure to provide a portable monitor further including a fluid component adjustment system configured to adjust a determined component content of the test fluid based on A) one or more physical properties of the test fluid and/or B) a component content of one or more components of the test fluid that have been at least partially determined by the first sensor arrangement and/or the second sensor arrangement. The fluid component adjustment system includes one or more of i) $H_2/CH_4$, $H_2/CO$, $H_2/H_2S$, and/or $H_2S/CO$ concentration correction tables, ii) $H_2/CH_4$, $H_2/CO$, $H_2/H_2S$, and/or $H_2S/CO$ correction curves, and/or iii) $H_2/CH_4$, $H_2/CO$, $H_2/H_2S$, and/or $H_2S/CO$ equations.

It is another and/or additional non-limiting object of the present disclosure to provide a portable monitor wherein the fluid component adjustment system is configured to provide a corrected $H_2$ and/or CO concentration values based on measured $H_2$, $CH_4$, CO, and/or $H_2S$ in the test fluid.

It is another and/or additional non-limiting object of the present disclosure to provide a portable monitor wherein the one or more physical properties of the test fluid include test fluid temperature and/or test fluid pressure.

It is another and/or additional non-limiting object of the present disclosure to provide a portable monitor that includes wireless technology to enable the handheld portable monitor to communicate with one or more remote systems selected from the group consisting of the internet, mobile phone systems, network computers, tablet computers, laptop computers, desktop computers, PDAs, and one or more separated components of the handheld portable monitor that are located remotely from one another.

It is another and/or additional non-limiting object of the present disclosure to provide a portable monitor including GPS software and hardware for obtaining GPS coordinates for the site to be tested or that has been tested.

It is another and/or additional non-limiting object of the present disclosure to provide a portable monitor that includes a RFID detection system and/or a barcode scanning system to identify the tested test site.

It is another and/or additional non-limiting object of the present disclosure to provide a portable monitor that includes a handheld portable control unit and a handheld portable measuring unit contained in separate housings. The handheld portable control unit is configured to monitor and/or control one or more functions of the handheld portable measuring unit, to be removably positioned at the tested test site, and to be physically removed from the test site after completion of the testing of the test site. The housing of the handheld portable measuring unit at least partially contains the first sensor arrangement and the second sensor arrangement. The handheld portable control unit is configured to not be required to be physically connected to the test site that while the handheld portable measuring unit is removably positioned at the test site during testing. The handheld portable measuring unit has a weight of less than 10 pounds and a volume of less than 300 cubic inches. The handheld portable control unit has a weight of less than 5 pounds and a volume of less than 100 cubic inches.

It is another and/or additional non-limiting object of the present disclosure to provide a method for using a handheld portable monitor to obtain and/or measure one or more properties of fluid at a test site. The method comprises: A)

providing a handheld portable monitor configured to enable a user to easily and conveniently carry the handheld portable monitor to a testing site and enable the user to monitor and/or obtain information about one of more properties of the fluid at the test site, and thereafter to enable the user to remove the handheld portable monitor from the test site, said handheld portable monitor having a total weight of less than 20 pounds and a total volume of less than 500 cubic inches and including one or more fluid connectors that enable the handheld portable monitor to test fluid at the test site and thereafter enable the handheld portable monitor to be removed from the tested test site after completion of testing, and including a sensor system to obtain and/or to measure one or more properties of the fluid located at the tested test site, the sensor system including a) first and second sample paths and b) a valve system that controls fluid flow between the first and second sample paths, a first sensor arrangement connected to the first sample path and a second sensor arrangement connected to the second sample path, the first sensor arrangement including a first hydrogen sensor and the valve system including a path valve; B) removably connecting the handheld portable monitor to the test site; C) measuring/determining one or more components of the test fluid at the test site; and wherein the valve system causing the valve to only allow the test fluid to flow through the first sample path when a hydrogen content in the test fluid as at least partially determined by the first hydrogen sensor is at or above a predetermined level; and wherein the valve system causing the path valve to allow the test fluid to flow through the second sample path when the hydrogen content in the test fluid as at least partially determined by the first hydrogen sensor is below the predetermined level.

It is another and/or additional non-limiting object of the present disclosure to provide a method for using a handheld portable monitor to obtain and/or measure one or more properties of fluid at a test site that further including the step of adjusting a determined component content of the test fluid based on A) one or more physical properties of the test fluid and/or B) a component content of one or more components of the test fluid that have been at least partially determined by the first sensor arrangement and/or the second sensor arrangement; the step of adjusting a determined component content including use of one or more of i) $H_2/CH_4$, $H_2/CO$, $H_2/H_2S$, and/or $H_2S/CO$ concentration correction tables, ii) $H_2/CH_4$, $H_2/CO$, $H_2/H_2S$, and/or $H_2S/CO$ correction curves, and/or iii) $H_2/CH_4$, $H_2/CO$, $H_2/H_2S$, and/or $H_2S/CO$ equations.

These and other advantages will become apparent to those skilled in the art upon the reading and following of this description taken together with the accompanying drawings.

BRIEF DESCRIPTION OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. Reference may now be made to the drawings, which illustrate various embodiments that the disclosure may take in physical form and in certain parts and arrangement of parts wherein:

FIG. 6 illustrates typical fermentation and methanogenesis reactions that occur in a landfill.

DESCRIPTION OF NON-LIMITING EMBODIMENTS

Figure 1:
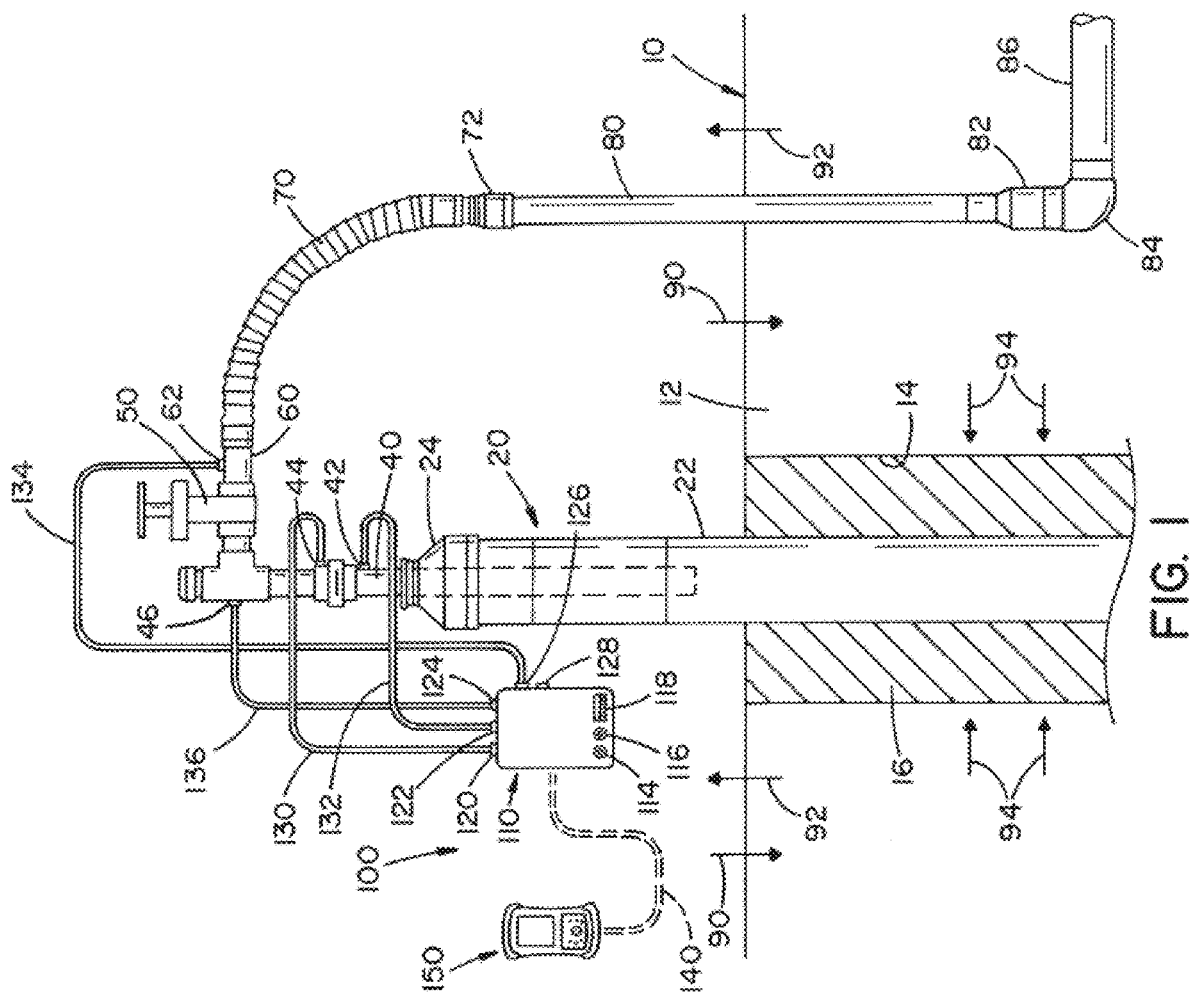
FIG. 1 is a schematic view of a landfill well being monitored by the portable monitor in accordance with the present disclosure.

A more complete understanding of the articles/devices, processes and components disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of" The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 inches to 10 inches" is inclusive of the endpoints, 2 inches and 10 inches, and all the intermediate values).

The terms "about" and "approximately" can be used to include any numerical value that can vary without changing the basic function of that value. When used with a range, "about" and "approximately" also disclose the range defined by the absolute values of the two endpoints, e g. "about 2 to about 4" also discloses the range "from 2 to 4." Generally, the terms "about" and "approximately" may refer to plus or minus 10% of the indicated number.

Various non-limiting embodiments of the present disclosure will now be described to provide an overall understanding of the principles of the structure, function, and use of the apparatus, systems and methods disclosed. Those of ordinary skill in the art will understand that apparatus, systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure. Any failure to specifically describe a combination or sub-combination of components should not be understood as an indication that any combination or sub-combination is not possible.

It will be appreciated that modifications to disclosed and described examples, arrangements, configurations, components, elements, apparatuses, devices, systems, methods, etc. can be made and may be desired for a specific application. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Referring now to the drawings wherein the showing is for the purpose of illustrating a non-limiting preferred embodiment of the disclosure only and not for the purpose of limiting the same, FIG. 1 illustrates a conventional landfill gas extraction system. As illustrated in FIG. 1, there is provided a landfill 10 containing waste 12. A well 20 is drilled into landfill 10. As can be appreciated, more than one well can be drilled in landfill 10. When more than one well is drilled in a landfill, two or more wells can be interconnected together by pipelines; however, this is not required.

The one or more wells 20 typically include one or more vertically-oriented pipes 22 installed in a well bore 14 in the waste of the landfill. Backfill 16 is typically inserted into the well bore after pipe 22 is inserted into the well bore. The depth of pipe 22 into the well bore and the number of wells formed in the landfill typically depends on the size and depth of the landfill. The one or more pipes 22 typically have perforations or slotted sections (not shown) disposed along the pipes and/or at or near the end portion of the pipes. As can be appreciated, the well can alternatively be formed of horizontal trenches or areas filled with gravel. These trenches or areas may be isolated from the atmosphere by a plastic liner or other impermeable barrier.

The top of well 20 includes a well header 24 on the top end of pipe 22. The top of header 24 includes an inlet pipe 40. The inlet pipe 40 extends through header 24 and partially into the top portion of pipe 22. The inlet pipe includes three side openings or ports 42, 44, 46. Openings 42 and 44 are pressure ports that enable pressure readings to be obtained. Pressure port 42 provides a pressure reading for the static pressure in well 20. The static pressure is also known as the applied vacuum to the well. This pressure port is located on the well side control valve and represents the actual pressure on the well. Pressure port 44 provides a pressure reading for the differential pressure. Differential pressure measures the pressure drop across and orifice or some other type of flow restrictor (not shown). The differential is a pressure that is taken downstream from pressure port 42. Opening 46 in the top portion of the inlet pipe allows for a temperature reading for the landfill gas being drawn into the well from the landfill. A wellhead valve 50 is connected to the top portion of inlet pipe 40. The wellhead valve controls the flow rate of landfill gas from the landfill into the well. Wellhead valve 50 typically includes a gate valve with an O-ring; however, this is not required. Connected to wellhead valve 50 is a pipe coupler 60 that includes a pressure port 62. Pressure port 62 is located downstream from the wellhead valve. Pressure port 62 provides a pressure reading for the available vacuum pressure that can be applied to the well. A flexible pipe portion 70 is secured to pipe coupler 60. Flexible pipe portion 70 is in turn connected to feed pipe 80 typically by a flexseal coupling 72 that is used to direct the landfill gas to a flare and/or a processing unit for further processing of the landfill gas. Feedpipe 80 typically is inserted to some depth in ground as illustrated in FIG. 1. Feedpipe 80 is commonly connected to a reducer 82 which in turn is connected at one end to an elbow 84. The outer end of elbow 84 is connected to pipe 86 that directs the landfill gas away from the landfill. A pump (not shown) is generally connected to pipe 86. The pump is used to apply a vacuum to the well. This vacuum can be measured by pressure port 62.

Landfill 10 typically includes one or more top layers (not shown) that are inserted over waste 12. The one or more top layers can include sand, dirt, gravel, etc. The one or more top layers can include one or more layers of materials (not shown) to at least partially entrap gases under the one or more top layers and/or control and/or reduce the flow rate of gases through the one or more top layers; however, this is not required.

The arrows in FIG. 1 illustrate the flow of gases into and out of a typical landfill 10. The arrows 90 pointing into the landfill illustrate air (e.g., oxygen, nitrogen, etc.) being drawn into the landfill. Arrows 92 pointing upward from the landfill illustrate landfill gas (e.g., methane, carbon dioxide, etc.) escaping the landfill through the one or more top layers of the landfill. The escape of landfill gas through the one or more top layers of the landfill can be partially the result of not enough landfill gas being drawn through pipe 22 of well 20. Arrows 94 pointing toward pipe 22 illustrate landfill gas being drawn into pipe 22. When too large a volume of landfill gas is drawn into well 20, the pressure differential between the landfill and atmosphere can result in air being drawn into the landfill as indicated by arrows 90. When air enters the landfill, anaerobic degradation of the waste in the landfill can be interrupted until the oxygen is consumed by aerobic processes. If very large quantities of air are introduced into the landfill, either through natural occurrence or overly aggressive operation of the landfill well, a partly unsupported subsurface combustion of the buried waste can be initiated. Such subsurface fires can be difficult to control or extinguish once started, and can also present health and safety hazards. The presence of carbon monoxide, carbon dioxide, and hydrogen sulfide in the landfill gas can be used as indicators of poorly supported combustion within the landfill. When too little of the landfill gases are drawn into the well 20, gas pressure builds up in the landfill and results in an increased rate at which the landfill gas passes through the one or more top layers of the landfill and into the atmosphere. As such, a "tradeoff" exists between extracting or "pulling" too high a flow rate of the landfill gas into the well and entraining excessive atmospheric air, and pulling too little landfill gas through the well and recovering less landfill gas and allowing more landfill gas to enter the atmosphere.

To collect the landfill gas from the landfill, the pressure in well 20 is reduced below that of the landfill gas in the landfill. The amount of "pull" exerted by the well on the landfill gas is controlled by operation of the blower and/or compressor (not shown) and/or by flow-controlling valves associated with the well. Reducing the pressure too much will tend to pull air through the top layer and into the landfill. However, the requisite amount of pull to cause air intrusion will vary due to a variety of factors including unknown local landfill gas generation rates and the consistency of the waste and soil in the landfill.

The portable monitor of the present disclosure is configured to provide the needed information to a field operator to enable the operator to adjust and control the flow rate of landfill gas into the landfill well to a) achieve a steady state of operation of the gas collection system, b) stabilize the rate and quality of extracted landfill gas, c) achieve and maintain effective subsurface gas migration control, d) achieve and maintain effective surface gas emissions control, e) assist with proper operation of control and recovery equipment, f) avoid well "over-pull" and maintain a healthy anaerobic state within the landfill, g) optimize landfill gas recovery for energy recovery purposes, h) control nuisance landfill gas odors, i) prevent or control subsurface landfill fires, j) protect structures on and near the landfill, and/or k) meet environmental and regulatory compliance requirements for landfills. Although the portable monitor is described with particular use and reference to landfill wells, it will be appreciated that the portable monitors can be used at other gas testing locations (e.g., biogas facilities, subterranean locations, other types of wells, etc.).

Individual landfill wells are periodically tested (e.g., monthly, quarterly, yearly, etc.) to determine the performance and status of the landfill well. After measurements are taken by the portable monitor of the present disclosure, the portable monitor is disconnected from the landfill well, adjustments (e.g., adjust flow rate, increase vacuum, etc.), if any, are made to the landfill well, and the portable monitor is moved to another landfill well to repeat the monitoring and measuring process for such other landfill well. This process is generally repeated for many different landfill wells located at the same and/or at different landfill sites.

Figure 2:
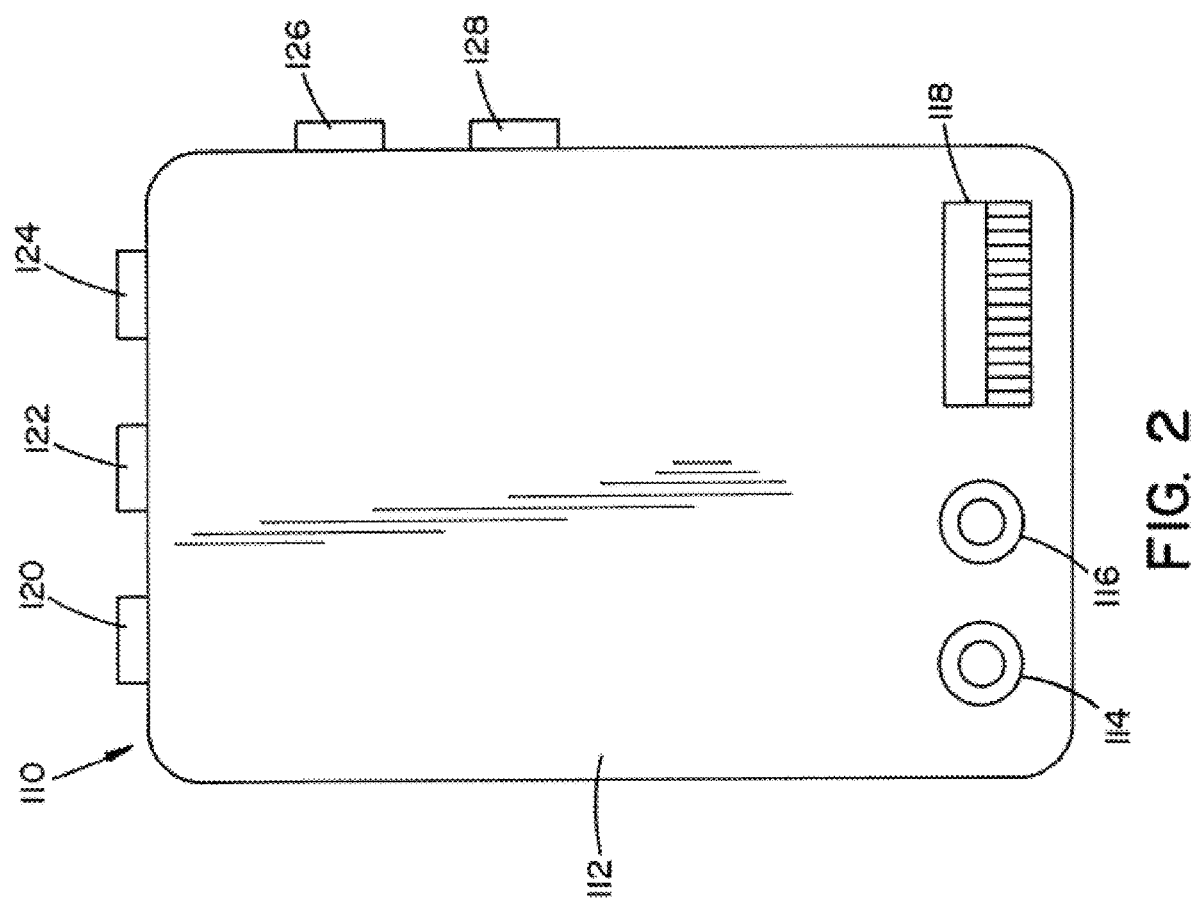
FIG. 2 is a top view of one non-limiting embodiment of a measuring unit of the portable monitor in accordance with the present disclosure.
Figure 3:
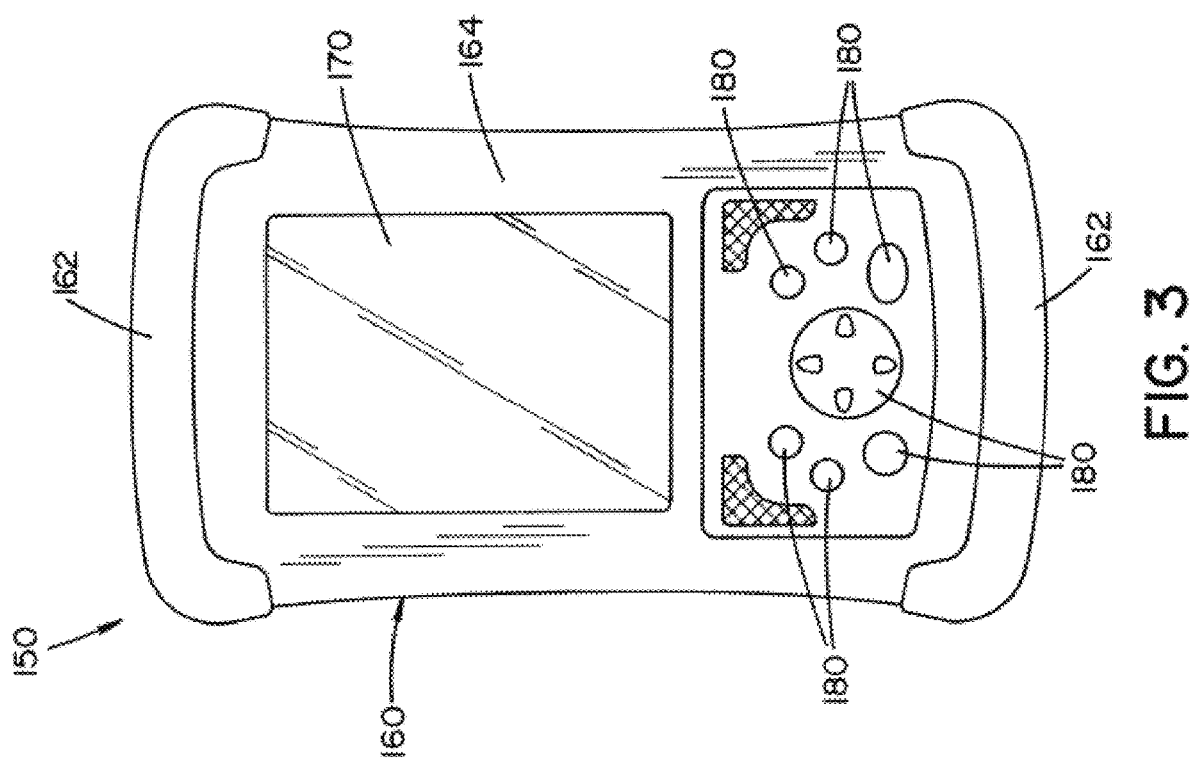
FIG. 3 is a top view of one non-limiting embodiment of a control unit of the portable monitor in accordance with the present disclosure.

Referring now to FIGS. 2-5, there are illustrated two non-limiting arrangements for portable monitor 100 in accordance with the present disclosure. Referring now to FIGS. 2 and 3, portable monitor 100 includes a measuring unit 110 and a control unit 150. Portable monitor 100 is configured to obtain various types of information from a plurality of different wells 20 so that the proper flow rate of landfill gas drawn into the wells from one or more landfills 10 can be obtained. FIG. 1 illustrates only one type of well to which the portable monitor can be temporarily connected to obtain information from the well. As can be appreciated, the portable monitor of the present disclosure can be connected to other types of landfill wells. The information that portable monitor 100 of the present disclosure can obtain from well 20 includes, but is not limited to, flow rate of landfill gas into the well, composition of the landfill gas flowing into the well, temperature of the landfill gas flowing into the well, LEL and/or UEL of the landfill gas being drawn into the well, differential pressure of the well, static pressure of the well, and/or available vacuum pressure for the well.

Referring now to FIG. 2, the measuring unit 110 of portable monitor 100 is a relatively small and light unit. Measuring unit 110 typically has a weight of less than about 5 lbs., and a total volume of less than about 200 cubic in. The housing 112 of the measuring unit is made of a durable material that protects the internal components of measuring unit 110 from damage. The measuring unit is configured to be used in a wide variety of environments. The measuring unit typically has an Ingress Protection Rating of at least IP67. The measuring unit is typically configured to operate in temperatures as low as about −20° F., and as high as about 120° F. The housing of the measuring unit can include one or more slots and/or connectors (not shown) to facilitate in removably connecting the housing to a well structure or the like so the measuring unit can be conveniently mounted in a temporary fashion during the testing of the landfill well; however, this is not required.

On the top face of housing 112 is an optional heat power button/indicator 114, a unit power button/indicator 116, and an optional battery life indicator 118. Unit power button/indicator 116 is used to manually power on or off the measuring unit. Unit power button/indicator 116 includes an indicator light to indicate when the measuring unit is powered on or off. The optional heat power button/indicator 114 is used to manually power on or off the optional heating system for the measuring unit. The heat power button/indicator (when used) includes an indicator light to indicate when the heating system is powered on or off. When the heat power button/indicator is activated, one or more heating elements in the measuring unit 110 supply heat to one or more regions of measuring unit 110. In colder temperatures, the operation of one of more components in measuring unit 110 can be impaired, thus resulting in slow or unreliable measurements from the landfill well. The one or more heating elements in measuring device 110 are configured to maintain the temperature of one or more internal components in the measuring device above a certain temperature. The optional battery life indicator 118 indicates the remaining charge of the rechargeable battery in the measuring unit.

On the sides of housing 112 are coupler ports 120, 122, 124, 126. Coupler port 120 is the static pressure port and is configured to be connected to a vacuum tube or fluid coupling device 130 which in turn is connected to pressure port 44 of inlet pipe 40 as illustrated in FIG. 1. Coupler port 122 is the impact pressure port and is configured to be connected to a vacuum tube or fluid coupling device 132 which in turn is connected to pressure port 42 of inlet pipe 40 as illustrated in FIG. 1. Coupler port 126 is the available pressure port and is configured to be connected to a vacuum tube or fluid coupling device 134 which in turn is connected to pressure port 62 of coupler pipe 60 as illustrated in FIG. 1. Coupler port 124 is a temperature port configured to connect to a temperature probe wire 136 which in turn is connected to a temperature probe located in opening 46 of inlet pipe 40 as illustrated in FIG. 1. The side of housing 112 also includes an exhaust port 128 to expel the analyzed landfill gas from the measuring unit. As can be appreciated, when portable monitor 100 is not used to test landfill wells, one or more of the coupler ports may not be used and/or can be eliminated from the portable monitor.

The measuring unit 110 is configured to use information received from coupler ports 120, 122 and 126 to determine the differential pressure of the well, static pressure of the well, and available vacuum pressure for the well. In one non-limiting arrangement, port 126 is also used to receive calibration gas and to receive gas/liquid samples from the well. Coupler port 124 is used by the measuring unit to determine the temperature of the landfill gas flowing into pipe 40. Portable monitor 100 can use these measurements from the measuring unit to calculate the flow rate of landfill gas into pipe 40. The measuring unit can include a single pressure sensor or a plurality of pressure sensors to measure the well pressures. In one non-limiting arrangement, measuring unit 110 includes three pressure sensors to enable the measuring unit to simultaneously measure the differential pressure of the well, static pressure of the well, and/or available vacuum pressure for the well; however, this configuration is not required.

In the inside of housing 112, there is provided a plurality of chemical analyzers to identify and/or measure the concentration of one or more components of the landfill gas. In particular, measuring unit 110 includes chemical analyzers to measure the concentration of one or more of methane, carbon dioxide, and oxygen and optionally or alternatively one or more of hydrogen, carbon monoxide, and/or hydrogen sulfide in the landfill gas. In one non-limiting arrangement. Measuring unit 110 includes a separate chemical analyzer to identify the presence and/or to calculate and/or measure the concentration of methane, a separate chemical analyzer to identify the presence and/or to calculate and/or measure the concentration of carbon dioxide, and a separate chemical analyzer to identify the presence and/or to calculate and/or measure the concentration of oxygen. In another non-limiting arrangement, measuring unit 110 includes a separate chemical analyzer to identify the presence and/or to calculate and/or measure the concentration of hydrogen, carbon monoxide, and/or hydrogen sulfide. As can be appreciated, measuring unit 110 can include more than three chemical analyzers when more than three different gases are to be identified and/or measured or calculated. For example, measuring unit 110 can include four or more chemical analyzers to also identify the presence and/or to calculate and/or measure the concentration of carbon monoxide, hydrogen, hydrogen sulfide, or nitrogen. As can be appreciated, other or additional gases can be identified and/or measured by the measuring unit. Generally, for each gas to be identified and/or measured or calculated, measuring unit 110 includes a separate chemical analyzer for such gas. The chemical analyzer for the methane and carbon dioxide is typically an IR measuring cell, and the chemical analyzer for oxygen is typically a galvanic cell; however, this is not required.

Measuring unit 110 includes one or more pumps to draw the landfill gas into one or more coupler ports 120, 122, 126, and/or expel the landfill gas through exhaust port 128. In addition to identifying and/or measuring the concentration of components of the landfill gas, the portable monitor can be used to measure the lower explosive limit (LEL) and/or upper explosive limit (UEL) of the landfill gas. Measuring unit 110 includes one or more circuits and/or microprocessors to operate one or more software and/or hardware programs in the measuring unit, and/or one or more components in the measuring unit (e.g., calibration hardware/software, flow rate calculation hardware/software, BTU calculation software, gas analysis hardware/software, communication hardware/software, pump, chemical analyzer, temperature detector, heating pad, thermocouple, etc.). The measuring unit can include one or more connection ports.

As illustrated in FIG. 1, there is provided a communication cable 140 to connect measuring unit 110 to the control unit 150 to enable data transfer between the two units. This cable connection arrangement between measuring unit 110 and control unit 150 is an optional arrangement. Measuring unit 110 can also include cable connection arrangements to connect to other types of devices (e.g., computer, phone, tablet, internet, printer, data storage, etc.). The measuring unit can optionally include wireless communication hardware to enable the measuring unit to communicate wirelessly with the control unit and/or one or more other devices.

Referring now to FIGS. 1 and 3, there is illustrated control unit 150 of portable monitor 100. Control unit 150 is a portable handheld device that is used to a) at least partially control the operation of measuring unit 110, b) to obtain and process information obtained/measured by measuring unit 110, and/or c) monitor the operation of measuring unit 100. As can be appreciated, control unit 150 can have other or additional uses. The communication between control unit 150 and measuring unit 110 is typically wireless; however, a cable connection using cable 140 as illustrated in FIG. 1 can be optionally used to connect control unit 150 and the measuring unit 110.

Control unit 150 is typically sized and configured like a typical PDA device, Palm PC device, smartphone, tablet, iPad, BLACKBERRY® device, virtual reality device, or augmented reality device; however, the control unit can be sized and configured in other ways. These types of devices are desirable due to their small, lightweight, and/or rugged configuration. Control unit 150 is configured for use in a wide variety of environments. Like measuring unit 110, control unit 150 typically has an Ingress Protection Rating of at least IP67 so the control unit can be safely used in rainy conditions, snowy conditions, sunny conditions, dusty conditions, etc. Control unit 150 is also typically configured to properly operate in temperatures at least as low as about 0° F., and at least as high as about 120° F. Control unit 150 typically has a weight and size that is less than measuring unit 110. Typically, control unit 150 has a weight of less than about 1.5 lbs. and a volume of less than about 50 cubic in.

As best illustrated in FIG. 3, non-limiting control unit 150 includes a housing 160 formed of a durable material such as, but not limited to, plastic, metal, etc. Located at the top and bottom of the housing are optional cushioning elements 162 configured to protect the housing and internal components of control unit 150 when the control unit is inadvertently dropped on the ground. The top face 164 of the housing includes an opening for viewing one or more display screens 170 (e.g., LED, QLED, Plasma, AMOLED, etc.). The one or more display screens 170 may be a black and white or a color display. One or more display screens 170 enable an operator to view various types of information. One or more display screens 170 may also include touch screen features to enable an operator to enter information into control unit 150 and/or access information from the control unit. A stylus pen or the like (not shown) may be used with the touch screen features of one or more display screens 170 to facilitate in the operation of control unit 150. The top face of control unit 150 also optionally includes several buttons 180 to operate one or more functions/features of control unit 150 (e.g., power on/off button, cursor button, function button, enter button, delete button, etc.). Control unit 150 may also include a display protector (not shown) that is removably fitted over the one or more display screens 170 to protect one or more display screens 170 from damage; however, this is not required. Control unit 150 can also include a hand strap and/or clip connector to facilitate in the carrying of the control unit; however, this is not required.

Control unit 150 includes one or more circuits and/or microprocessors to operate one or more software and/or hardware programs loaded in the control unit. For example, the control unit may include one or more processors in combination with various amounts of data storage memory. An operating system (e.g., Microsoft Windows Mobile software, Linux, Android, Appeal iOS, etc.) can be loaded in the control unit. Various other types of software can be loaded in control unit 150 to enhance the features/operation of the control unit. Such software can include, but is not limited to, GPS software and/or firmware, navigation software and/or firmware, wireless communication software and/or firmware, photograph/video software and/or firmware, sound/music software and/or firmware, sound recording software and/or firmware, voice recognition software and/or firmware, file/data transfer software and/or firmware, internet browser software and/or firmware, word processor software and/or firmware, touch screen software and/or firmware, database software and/or firmware, spreadsheet software and/or firmware, operating system software and/or firmware, scanner software and/or firmware, printer software and/or firmware, power point software and/or firmware, CAD software and/or firmware, email software and/or firmware, calendar software and/or firmware, address book software and/or firmware, security software and/or firmware, t.v. software and/or firmware, radio software and/or firmware, data management software and/or firmware, software and/or firmware to operate/monitor the measuring unit of the portable monitor, calibration software and/or firmware for the control unit and/or measuring unit, handwriting recognition software and/or firmware, diagnostic software and/or firmware for the control unit and/or measuring unit, time/date/timer software and/or firmware, software and/or firmware to make recommendations for landfill gas flow rate into well, BTU calculation software and/or firmware, LEL calculation software and/or firmware, EPA software and/or firmware, environmental software and/or firmware, software and/or firmware used to process landfill well or testing location data, software and/or firmware to process gas data, software and/or firmware to process liquid data, software and/or firmware to process flow rates, software and/or firmware to process temperature determinations, temperature control software and/or firmware, GPS software and/or firmware, file management software and/or firmware, office type software and/or firmware, communication software and/or firmware, calibration software/firmware, and the like.

Control unit 150 also optionally includes software that is used to calibrate, diagnose problems, control and/or monitor measuring unit 110, and/or to receive and/or transmit information between the control unit and measuring unit. Control unit 150 may also include software to process the information received from measuring unit 110 to provide additional information about the landfill well. The control unit also includes wireless technology to transfer information between the control unit and the measuring unit (e.g., 802.11 wireless technology, Bluetooth® technology, IR technology, etc.). The control unit can include other optional components such as, but not limited to, camera, microphone, speaker, indicators (e.g., battery level indicator, on/off indicator, chemical analyzer replacement notification, fluid filter replacement notification, chemical analyzer malfunction or damage, improper installation or missing chemical analyzer, improper installation or missing fluid filter, etc.), power pack compartment used to store one or more rechargeable energy cells, one or more connection ports (e.g., fire wire, USB, serial cable, phone cable, ethernet cable, etc.), and/or one or more expansion slots (e.g., Type1 and/or Type II expansion slots), etc.

In operation, control unit 150 can be used to control most, if not all, of the operations of measuring unit 110 once the measuring unit has been connected to the landfill well. As such, an operator is able to remotely monitor and/or control the measuring unit. This is a significant improvement over prior art portable monitors wherein the operator had to be positioned next to the single portable monitor in order to monitor the operation of the single portable monitor, control the operation of the single portable monitor, and to take measurements from the single portable monitor. As can be appreciated, the portable monitor can optionally include a single housing that includes both the control unit and the measuring unit to form a single unit.

Figure 4:
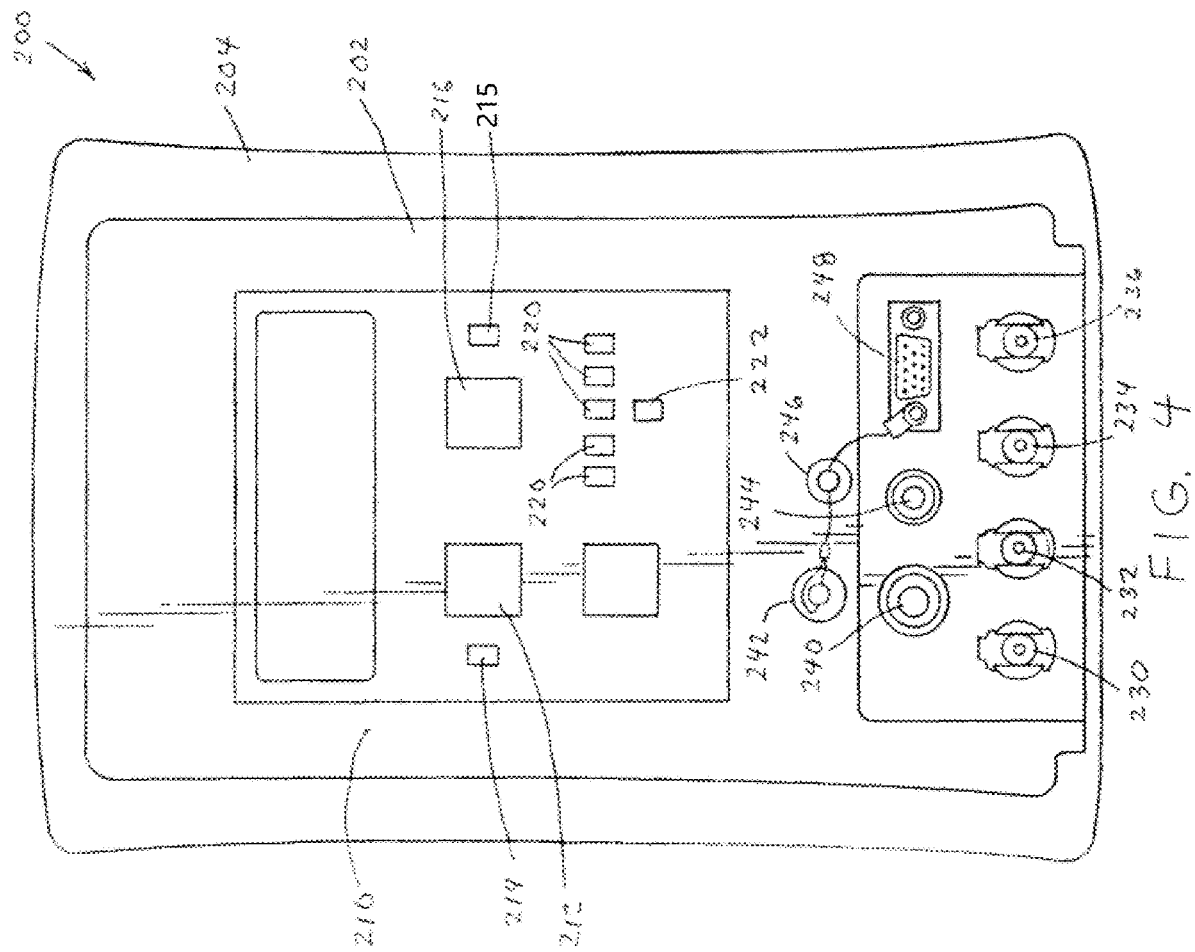
FIG. 4 is a top view of another non-limiting embodiment of a measuring unit of the portable monitor in accordance with the present disclosure.

Referring now to FIG. 4, another non-limiting embodiment of the measuring unit 200 of portable monitor 100 is illustrated. Measuring unit 200 is a relatively small and light unit, typically having a weight of less than about 5 lbs., and a total volume of less than about 200 cubic inches. The housing 202 of measuring unit 200 is made of a durable material that protects the internal components of measuring unit 200 from damage. A protective material 204 can be positioned about all or a portion of the top, bottom and side edges of housing 202 to provide additional protection to the housing; however, this is not required. Protective material 204 can be formed of rubber, plastic, foam, etc. Generally, protective material 204 is a durable and flexible material that can absorb a force that is applied to housing 202, such as an object bumping into the housing or measuring unit 200 being dropped on the ground. Measuring unit 200 is configured to be used in a wide variety of environments. Measuring unit 200 typically has an Ingress Protection Rating of at least IP67. Measuring unit 200 is typically configured to operate in temperatures as low as about −20° F., and as high as about 120° F. The housing of measuring unit 200 can include one or more slots and/or connectors (not shown) to facilitate in removably connecting the housing to a well structure or the like so that measuring unit 200 can be conveniently mounted in a temporary fashion during the testing the landfill well; however, this is not required.

The top face 210 of housing 202 includes several buttons, light indicators, ports, etc. As can be appreciated, the location of one or more buttons, light indicators, ports, etc., on housing 202 is non-limiting. As illustrated in FIG. 4, the front or top face of the housing includes a power button 212. A light 214 (e.g., LED light, etc.) is positioned next to the power button; however, this is not required. The light can be used to indicate whether the power to the measuring unit has been activated or deactivated. The front or top face of the housing optionally includes a Bluetooth® button 216. A light 215 (e.g., LED light, etc.) is positioned next to the optional Bluetooth® button; however, this is not required. Light 215 can be used to indicate whether the Bluetooth® feature has been activated or deactivated, and/or can be used to indicate whether a Bluetooth® connection has been established. The front or top face of housing 202 optionally includes several optional lights 220 (e.g., LED lights, etc.) which are used to indicate the power level of the power source for the measuring unit. Optional lights 220 can be different colored lights to indicate different power levels; however, this is not required. As can be appreciated, other indicators can be used to indicate power level. The front or top face of housing 202 includes an optional light 222 (e.g., LED light, etc.) to indicate whether the power source of the measuring unit is being charged; however, this is not required. As can be appreciated, one or more of the above-mentioned buttons and/or lights can be replaced by a screen and/or touch screen arrangement. When a screen and/or a touch screen is used, additional features can be accessed and/or displayed on such screen and/or touch screen arrangement (e.g., status of one or more pressure sensors, status of one or more pumps, status of one or more chemical analyzers, status of one or more fluid filters, status of one or more heating pads, status of one or more thermocouples, status of data transfer between the measuring unit and control unit or some other unit, exterior temperature, temperature of one or more components in the housing, temperature in the housing, malfunction or error status, testing status, information about components in the measuring unit, information about software used in the measuring unit, power level status, Bluetooth® status, GPS information, etc.). As can be appreciated, one or more types of the information listed above and/or other types of information can be alternatively or additionally sent to control unit 150 for display on the control unit; however, this is not required.

The bottom portion of the front or top face of housing 202 optionally includes four gas/liquid ports 230, 232, 234, 236. Port 230 is an exhaust port and is used to exhaust gases/liquids that were previously drawn into the measuring unit via ports 232, 234 and/or 236. Port 232 is a port that is to be connected to the well via a tube to measure the available (system) vacuum being applied to the well. Port 234 is port that is to be connected to the well via a tube to measure the differential pressure on the well. Port 234 is also referred to as the impact port. Port 236 is a port that is to be connected to the well via a tube so as to measure the static wellhead pressure of the well. Ports 232, 234 and/or 236 can also be used to calibrate one or more components in the measuring unit (e.g., pressure sensors, chemical analyzers, etc.) and/or be used to draw samples of gas/liquid from the well into the measuring unit; however, this is not required. In one non-limiting arrangement, port 236 is also used to receive calibration gas and to receive gas/liquid samples from the well. As can be appreciated, the measuring unit can include a fewer number of ports or additional ports (e.g., sample port, calibration port, etc.).

The bottom portion of the front or top face of housing 202 optionally includes a charge port 240 that is used to charge the power source in measuring unit 200. A removable cap 242 is optionally used to protect charge port 240. The bottom portion of the front or top face of housing 202 optionally includes a thermistor port 244 and a cap 246. The thermistor port houses a resistor that prevents overheating or other types of damage to the electrical components in the measuring unit. The bottom portion of the front or top face of the housing optionally includes a communication port 248 (e.g., USB port, serial port, firewire port, etc.) that can be used to connect a commination cable to the measuring unit so data can be transferred from and/or to the measuring unit. As illustrated in FIG. 4, the communication port is in the form of a serial port; however, this is not required. As can be appreciated, data to and/or from the measuring unit can be transferred/received wirelessly; however, this is not required.

The measuring unit includes at least three chemical analyzers to identify and measure the amount of at least three components in a sampled fluid (e.g., methane, oxygen, carbon dioxide, carbon monoxide, hydrogen, hydrogen sulfide, etc.) being drawn from the landfill well. The measuring unit can optionally include two or more infrared gas analyzers, one each to identify and measure methane and carbon dioxide. Three or more different gases can be identified and/or measured by the measuring unit of the present disclosure. The measuring unit can optionally include one or more analyzers (e.g., electrochemical cell, infrared cell, TDL (laser) and UV absorption spectroscopy, thermal-conductivity detection, etc.) to identify and measure oxygen. As can be appreciated, different types of gas analyzers can be used to identify and measure the methane, carbon dioxide, oxygen, hydrogen, hydrogen sulfide, and/or carbon monoxide in the fluid stream flowing through the landfill well; however, this is not required. As can also be appreciated, one or more additional chemical analyzers can be used to identify and measure other gases in the fluid stream; however, this is not required. If more than three chemical analyzers are included in the measuring unit, then the measuring unit can be used to identify and/or measure more than three different components in a sampled fluid. In addition to the identifying and/or measuring the concentration of components of the landfill fluid, the measuring unit and/or control unit can optionally be used to calculate and/or measure the lower explosive limit (LEL) and/or upper explosive limit (UEL) of the landfill fluid.

The measuring unit optionally includes one or more pressure sensors. In one non-limiting arrangement, the measuring unit includes at least three pressure sensors to be able to measure up to three different pressures on the landfill well. In another non-limiting arrangement, the measuring unit includes more than three pressure sensors (e.g., four, five, six, etc.). The additional pressure sensors can be used to enable the measuring unit to measure more than three different pressures from the landfill well; however, this is not required. Alternatively or additionally, the one or more additional pressure sensors can be used to obtain more accurate pressure readings. For example, the measuring unit can include one or more pressure sensors configured for use within a certain pressure range. As such, the measuring unit can include a logic circuit and/or microprocessor to activate/deactivate certain pressure sensors and/or direct fluid to certain pressure sensors based on a detected fluid pressure so a certain pressure sensor that is configured to accurately measure pressure within a certain pressure range is used to measure the fluid pressure. In one non-limiting arrangement, the measuring unit includes five pressure sensors and at least two of the pressure sensors are configured to have a preferred pressure measuring range that is different from the preferred pressure measuring range of at least two, and typically three of the other pressure sensors. As can be appreciated, for some landfill well measurements and/or for other types of testing locations (e.g., biogas facility, etc.), less than three pressure sensors may be needed.

The measuring unit generally includes one or more pumps used to draw fluid into the measuring unit and expel fluid from the measuring unit. As can be appreciated, the measuring unit can include a plurality of pumps.

The measuring unit optionally includes one or more heating elements or pads configured to maintain a minimum temperature of the components within the housing of the measuring unit. One or more temperature sensors (e.g., thermocouples, etc.) are optionally positioned in the interior of the housing to obtain temperature readings in various regions of the housing interior. Generally, the temperature sensors (when used) are positioned on or near important components in the housing (e.g., pressure sensors, pump, chemical analyzers, microprocessor, etc.). The temperature sensors can be used to activate/deactivate one or more of the heating elements or pads in the housing. A resistor and/or microprocessor can optionally be used to activate/deactivate one or more of the heating elements or pads. In one non-limiting arrangement, a microprocessor is used to activate/deactivate one or more of the heating elements or pads in the housing based on a low and/or high threshold temperature detected by one or more of the temperature sensors. For example, if the microprocessor receives information from one or more of the temperature sensors that a temperature is at or below a certain low threshold temperature, the microprocessor causes one or more of the heating elements or pads to be activated. If the microprocessor receives information from one or more of the temperature sensors that a temperature is at or above a certain high threshold temperature, the microprocessor causes one or more of the heating elements or pads to be deactivated. In another non-limiting arrangement, the interior of the housing of the measuring unit includes N number of temperature sensors wherein N is three or more in value. The microprocessor is configured to cause all or a majority of the heating elements or pads in the housing to be activated when the microprocessor receives information from a majority or all of the N number of temperature sensors that a temperature is at or below a certain low threshold temperature. Also, the microprocessor is configured to cause all or a majority of the heating elements or pads in the housing to be deactivated when the microprocessor receives information from a majority or all of the N number of temperature sensors that a temperature is at or above a certain high threshold temperature. The control of the heating pads can be from one or more microprocessors in the measuring unit and/or from one or more microprocessors in the control unit.

The measuring unit includes one or more circuits and/or microprocessors to operate one or more software and/or hardware programs in the measuring unit, and/or one or more components in the measuring unit (e.g., calibration hardware/software, flow rate calculation hardware/software/firmware, BTU calculation software, gas analysis hardware/software/firmware, communication hardware/software, mode of operation hardware/software, pump, chemical analyzer, temperature detector, composition calibration software/firmware, heating pad, thermocouple, etc.).

The measuring unit can optionally include one or more filters to inhibit or prevent materials other than fluid and/or other components in the sampled fluid from contacting one or more chemical analyzers and/or pressure sensors. Foreign material (e.g., dirt, solid particles, etc.) can damage and/or interfere with the proper operation of the chemical analyzers and/or pressure sensors. Also, for some chemical analyzers, some components in the sampled fluid can interfere with proper readings and/or can damage or contaminate a chemical analyzer. In one non-limiting arrangement, the measuring unit includes one or more filters to partially or fully remove foreign materials from a sampled fluid, and/or one or more fluid filters to partially or fully removed one or more components of the sampled fluid prior to one or more chemical analyzers measuring a component of the sampled fluid. The one or more filters (e.g., foreign material filer, fluid filter for partial or full removal of one or more components from the sampled fluid) can be configured to be replaced. The measuring unit can include a display and/or send information to the control unit to inform a user when to replace one or more filters; however, this is not required.

Figure 9:
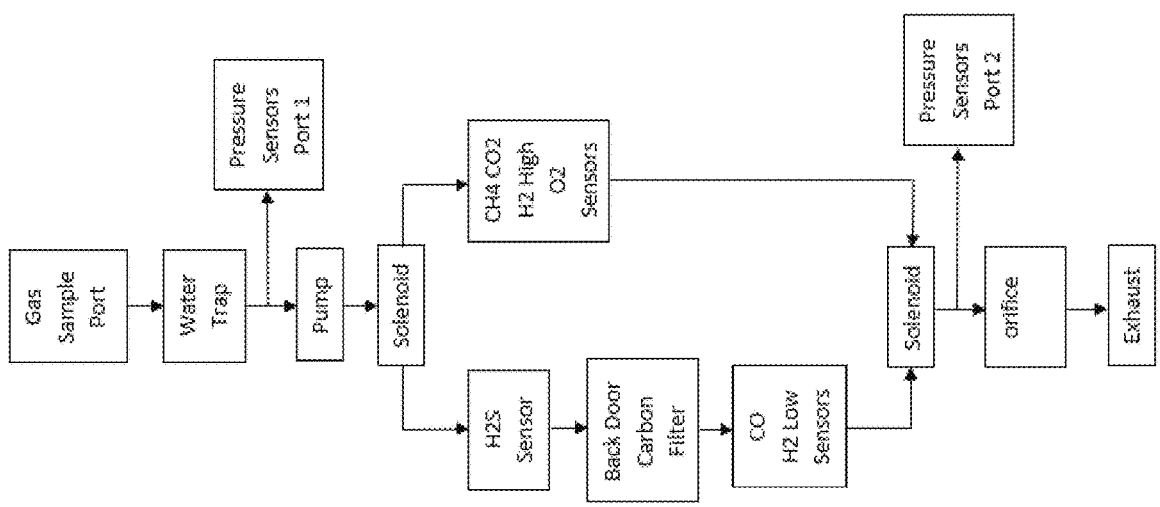
FIG. 9 is a flow chart of one non-limiting operation of the portable monitor in accordance with the present disclosure.

Referring now to FIG. 9, a non-limiting flow chart of the operation of the measuring unit is illustrated. As illustrated in FIG. 9, the measuring unit includes two sample paths that are isolated from one another by a valve system (e.g., two or more solenoid valves, two or more manual valves, etc.). Sample Path 1 is configured to measure methane, oxygen, hydrogen, and/or carbon dioxide levels in the sampled fluid. Sample Path 2 is configured to measure hydrogen, carbon monoxide, and/or hydrogen sulfide. The measuring unit can be configured to not allow sampled fluids to flow into Sample Path 2 if the hydrogen content measured in Sample Path 1 is above some predefined level. However, once the sampled fluids are allowed to flow into Sample Path 2, the measuring unit can be configured to allow the sampled fluid a) be fully diverted to Sample Path 2 thereby eliminating further flow through Sample Path 1, or b) be allowed to flow through both Sample Path 1 and 2. When the sampled fluid is allowed to simultaneously flow through both Sample Paths 1 and 2, the chemical sensors/analyzers in both Sample Paths 1 and 2 can optionally simultaneously measure/detect/analyze the components of the sampled fluid.

The measuring unit can optionally be configured to measure the $H_2$ levels in the sampled fluid. The measuring unit can be configured to measure both low and high levels of $H_2$ in the fluid. The ability to accurately determine $H_2$ levels in a gas sample is a potentially valuable tool to monitor the status of the fermentation process and methanogenesis reactions at ETLF facilities.

The measuring unit can use a multipath fluid flow system as illustrated in FIG. 9 to protect certain types of sensors from damage, contamination, or producing unreliable readings for certain components in a fluid sample. Chemical sensors/analyzers for components such as carbon monoxide and hydrogen sulfide are susceptible to being contaminated by hydrogen. Hydrogen levels in a fluid sample that exceed 1-2 vol. % can contaminate the chemical sensors/analyzers for carbon monoxide and hydrogen sulfide, thereby making such chemical sensors/analyzers inoperable, unusable, and/or result in false/inaccurate readings. The measuring unit can be configured to use multiple fluid flow paths that isolate chemical sensors/analyzers for carbon monoxide and/or hydrogen sulfide from the sampled fluid stream until the hydrogen content of the sampled fluid stream can be determined safe for analysis by such sensors. If the hydrogen content in the sampled stream is determined to be lower than or at a certain or predetermined amount or level, the measuring unit can then optionally direct at least a portion of the sampled fluid stream to the chemical sensors/analyzers for carbon monoxide and/or hydrogen sulfide so that such chemical sensors/analyzers can accurately measure the content of carbon monoxide and/or hydrogen sulfide in the sampled fluid stream without damaging and/or contaminating the chemical sensors/analyzers for carbon monoxide and/or hydrogen sulfide. However, if the hydrogen level of the sampled fluid stream is found to be too high or at or above a predetermined level, the measuring unit can keep the chemical sensors/analyzers for carbon monoxide and/or hydrogen sulfide isolated from the sampled fluid stream not damage and/or contaminate the chemical sensors/analyzers for carbon monoxide and/or hydrogen sulfide.

The isolation of the chemical sensors/analyzers for carbon monoxide and/or hydrogen sulfide can be accomplished by one or more manual valves (e.g., manually openable and closeable valve, ball valves, butterfly valves, globe valves, gate valves, diaphragm valves, etc.) or controlled valves (e.g., solenoid valve, motorized valve, hydraulic valve, linear motion valve, rotary motion valve, etc.).

Referring again to FIG. 9, the measuring unit 200 includes a Gas Sample Port 126, 236 that enables the measuring unit to receive a gas/liquid sample from a test site.

The measuring unit can optionally include a Water Trap to remove water from the gas/liquid sample. Excessive amounts of water in the gas/liquid sample can interfere with the proper measurement of one or more components in the gas/liquid sample by the one or more sensors in the measuring unit.

A Pressure Sensor (e.g., Pressure Sensors Port 1) can optionally be used to measure the pressure of the gas/liquid sample that enters the measuring unit. Such information can be used to provide information about the test site and/or to facilitate in the measurement of components in the gas/liquid sample by the measuring unit.

A Pump is generally used to move the gas/liquid sample into Sample Paths 1 and/or 2 of the measuring unit. The Pump can optionally be used to draw the gas/liquid sample into the measuring device via the Gas Sample Port.

The measuring unit includes one or more valves (e.g., Solenoid or other controllable valve, manual valve, etc.) to control the fluid path of the gas/liquid sample through the measuring unit. FIG. 9 illustrates the valve as a Solenoid valve. In one non-limiting configuration, the one or more valves are solenoid valves or other controllable valves. The use of the one or more valves in the measuring unit are used to protect chemical sensors/analyzers from damage by a partially high level of $H_2$ in the gas/liquid sample.

In one non-limiting arrangement, the measuring unit has the one or more valves initially direct the gas/liquid sample into Sample Path 1 to be analyzed by one or more chemical sensors/analyzers (e.g., electrochemical cell, infrared cell, TDL (laser) and UV absorption spectroscopy, thermal-conductivity detection, etc.). As illustrated in FIG. 9, Sample Path 1 includes a sensor to measure concentrations of $H_2$ and optionally one or more of $CH_4$, $CO_2$, $O_2$ in the gas/liquid sample. Sample Path 1 can include one chemical sensor/analyzer or a plurality of chemical sensors/analyzers, depending on the type of component in the gas/liquid sample to be analyzed and/or the number of components in the gas/liquid sample to be analyzed.

In one non-limiting configuration of the measuring unit, the concentration of $H_2$ in the gas/liquid sample can be determined by a single $H_2$ sensor.

In another non-limiting configuration of the measuring unit, the concentration of $H_2$ in the gas/liquid sample can be determined by both a $H_2$ sensor and a $CH_4$ sensor. It has been found that concentration of $H_2$ in the gas/liquid sample (when only determined by a single $H_2$ sensor) can provide a false reading when there are elevated levels of $CH_4$ in the gas/liquid sample. When both the $H_2$ and $CH_4$ concentrations are measured, $CH_4$ value compensation calculations can optionally be used to adjust the measured levels of $H_2$ to calculate a corrected $H_2$ concentration in the gas/liquid sample. The measuring unit and/or the control unit can optionally include $H_2/CH_4$ concentration correction tables, correction curves, and/or equations to provide a corrected $H_2$ concentration value based on the measured $H_2$ and $CH_4$ in the gas/liquid sample.

In another non-limiting configuration, the concentration of $H_2$ in the gas/liquid sample can be determined by first determining the concentration of $CH_4$ in the gas/liquid sample. In such a non-limiting configuration, the one or more valves in the measuring unit initially direct the gas/liquid sample to Sample Path 1.

Once the concentration of $H_2$ in the gas/liquid sample is determined to be below some predefined concentration, the one or more valves (e.g., solenoid valve or other controllable valve, etc.) in the measuring device are configured to allow the gas/liquid sample to flow through Sample Path 2 to be further analyzed by one or more other chemical sensors/analyzers (e.g., electrochemical cell, infrared cell, TDL (laser) and UV absorption spectroscopy, thermal-conductivity detection, etc.) that are located in Sample Path 2. For example, if it is determined that that the concentration of $H_2$ in the gas/liquid sample is less than 2 vol. % based on the analysis of the gas/liquid sample in Sample Path 1, then the one or more valves can be configured to open/close to allow the gas/liquid sample to flow into Sample Path 2. However, if the concentration of $H_2$ in the gas/liquid sample is determined to be at or above some predefined concentration, then the one or more valves can be configured to continue to prevent the gas/liquid sample from flowing into Sample Path 2.

If the $H_2$ concentration of the concentration of in the gas/liquid sample is determined to be at or above some predefined concentration, then 1) all or a portion of the gas/liquid sample is expelled from the measuring unit via the Exhaust Port, and/or 2) at least a portion of the gas/liquid sample is saved in a sampling container for later testing for other gas components in the gas/liquid sample (e.g., hydrogen sulfide, carbon monoxide, etc.). As illustrated in FIG. 9, one or more valves (e.g., solenoid valve or other controllable valve, etc.) in the measuring device are configured to allow the gas/liquid sample to flow out of Sample Path 1, optionally through an Orifice, and out of the measuring device via the Exhaust Port. As the gas/liquid sample flows toward the Exhaust Port, the pressure of the gas/liquid sample can optionally be measured by a Pressure Sensor (e.g., Pressure Sensors Port 2). FIG. 9 illustrates the valve as a Solenoid valve.

Sample Path 2 can include sensors such as a carbon monoxide sensor, a hydrogen sulfide sensor, and/or one or more other or additional sensors. Generally, the one or more sensors used in Sample Path 2 could provide false readings and/or could be damaged when there is a too high concentration of $H_2$ in the gas/liquid sample.

After one or more of the components of the gas/liquid sample are analyzed by the one or more other chemical sensors/analyzers located in Sample Path 2, the gas/liquid sample can be expelled from Sample Path 2 via one or more one or more valves (e.g., solenoid valve or other controllable valve, etc.) in the measuring device, and optionally through an Orifice, and out of the measuring device via the Exhaust Port.

The measuring unit and/or the control unit can be optionally configured to determine a Balance Gas Value of the gas/liquid sample. For example, Balance Gas Value could be equal to 100% minus the component volume of the one or more components analyzed in Sample Path 1. The Balance Gas Value could optionally be used to determine whether or not the gas/liquid sample is allowed to flow through Sample Path 2.

As illustrated in FIG. 9, Sample Path 2 includes one or more chemical sensors/analyzers that can be used to measure levels of $H_2$, CO, and/or $H_2S$ in the gas/liquid sample. In one non-limiting configuration, the Sample Path 2 of the measuring unit is a chemical analyzer for hydrogen sulfide and one or more separate chemical analyzers for carbon monoxide and/or hydrogen.

As illustrated in FIG. 9, the chemical analyzer for hydrogen sulfide is optionally positioned upstream to the one or more chemical analyzers for carbon monoxide and/or hydrogen such that hydrogen sulfide concentrations in the gas/liquid sample are measured prior to the measurement of carbon monoxide and/or hydrogen in the gas/liquid sample. The hydrogen sulfide in the gas/liquid sample can potentially interfere with accurate concentration analysis by the one or more chemical analyzers for low levels of hydrogen in the gas/liquid sample.

Sample Path 2 can optionally include a Back Door Carbon Filter to partially or fully remove $CH_4$ and/or $CO_2$ from the gas/liquid sample. $H_2S$, $CH_4$, and/or $CO_2$ in the gas/liquid sample can potentially interfere with accurate concentration analysis by the one or more chemical analyzers for carbon monoxide and/or low levels of hydrogen in the gas/liquid sample. Also, some chemical analyzers for CO and/or $H_2$ can be damaged or fouled by the presence of $H_2S$ in the gas/liquid sample.

The control unit and/or measuring unit can optionally use the detected amounts of $H_2S$, $H_2$, $CH_4$, and CO to make adjustments to the concentration levels of $H_2$ and/or CO in the gas/liquid sample. $H_2S$ and/or $CH_4$ in the gas/liquid sample can interfere with accurate measurements of $H_2$ in the gas/liquid sample. As such, the measuring unit and/or the control unit can optionally include $H_2/CH_4$ and/or $H_2/CO$ and/or $H_2/H_2S$ and/or $H_2S/CO$ concentration correction tables, correction curves, and/or equations to provide a corrected $H_2$ and/or CO concentration values based on the measured $H_2$, $CH_4$, CO, and/or $H_2S$ in the gas/liquid sample. The control unit and/or measurement unit can optionally include software and/or firmware to adjust the $H_2$ and/or CO measured concentration values based on certain measured levels of $H_2$, $CH_4$, CO, and/or $H_2S$ in the gas/liquid sample.

Figure 5:
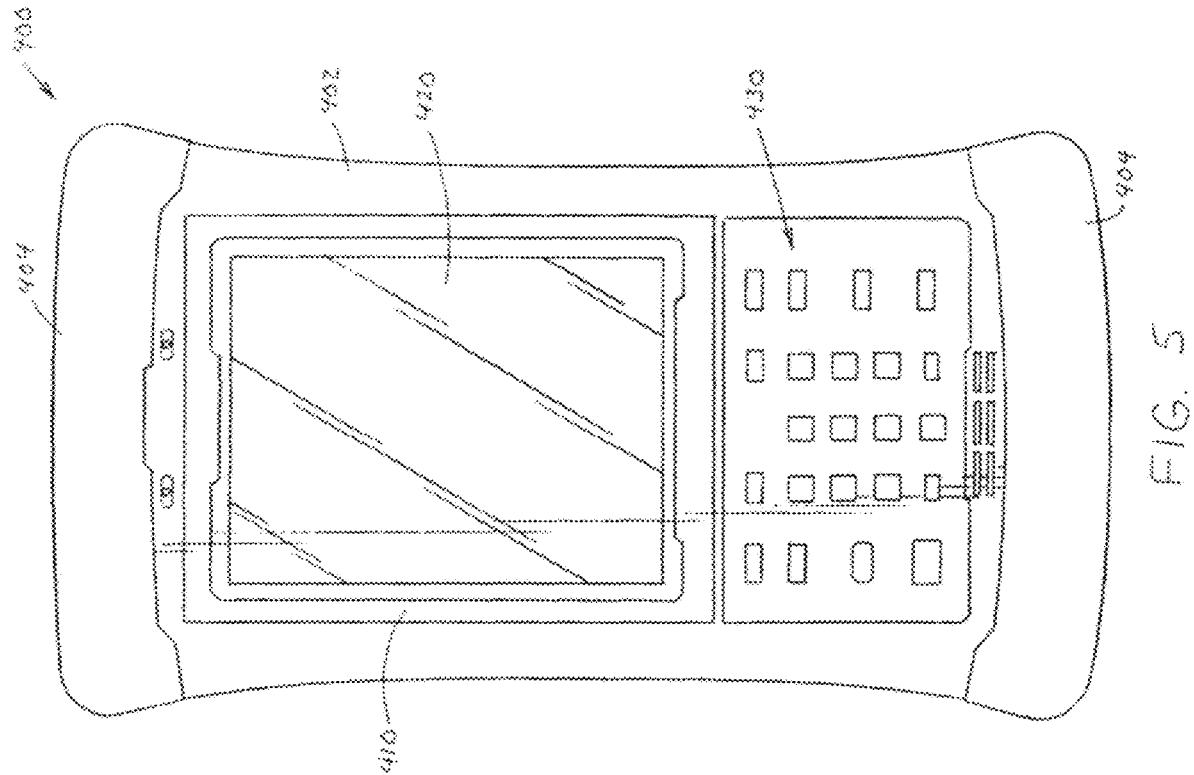
FIG. 5 is a top view of another non-limiting embodiment of a control unit of the portable monitor in accordance with the present disclosure.
Figure 7:
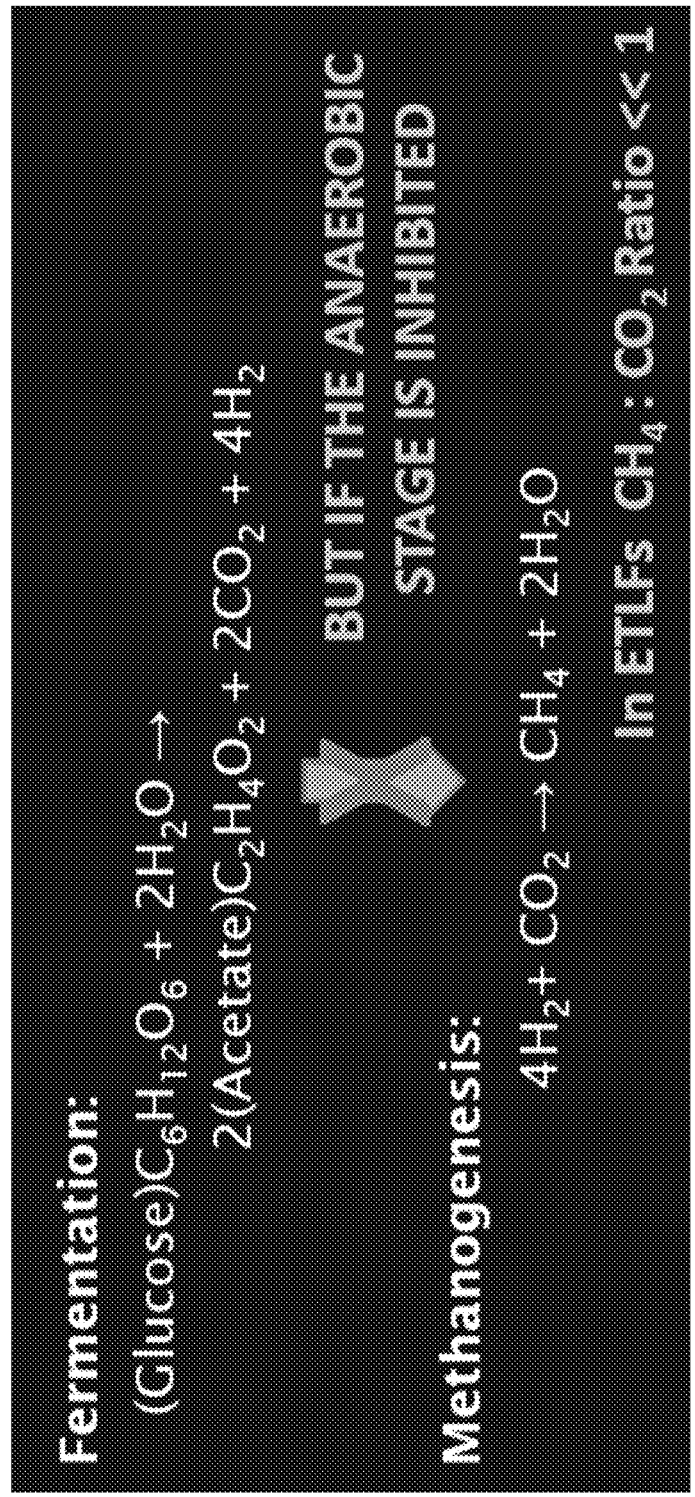
FIG. 7 illustrates fermentation and methanogenesis reactions that occur in a landfill wherein the methanogenesis reaction in inhibited.
Figure 8:
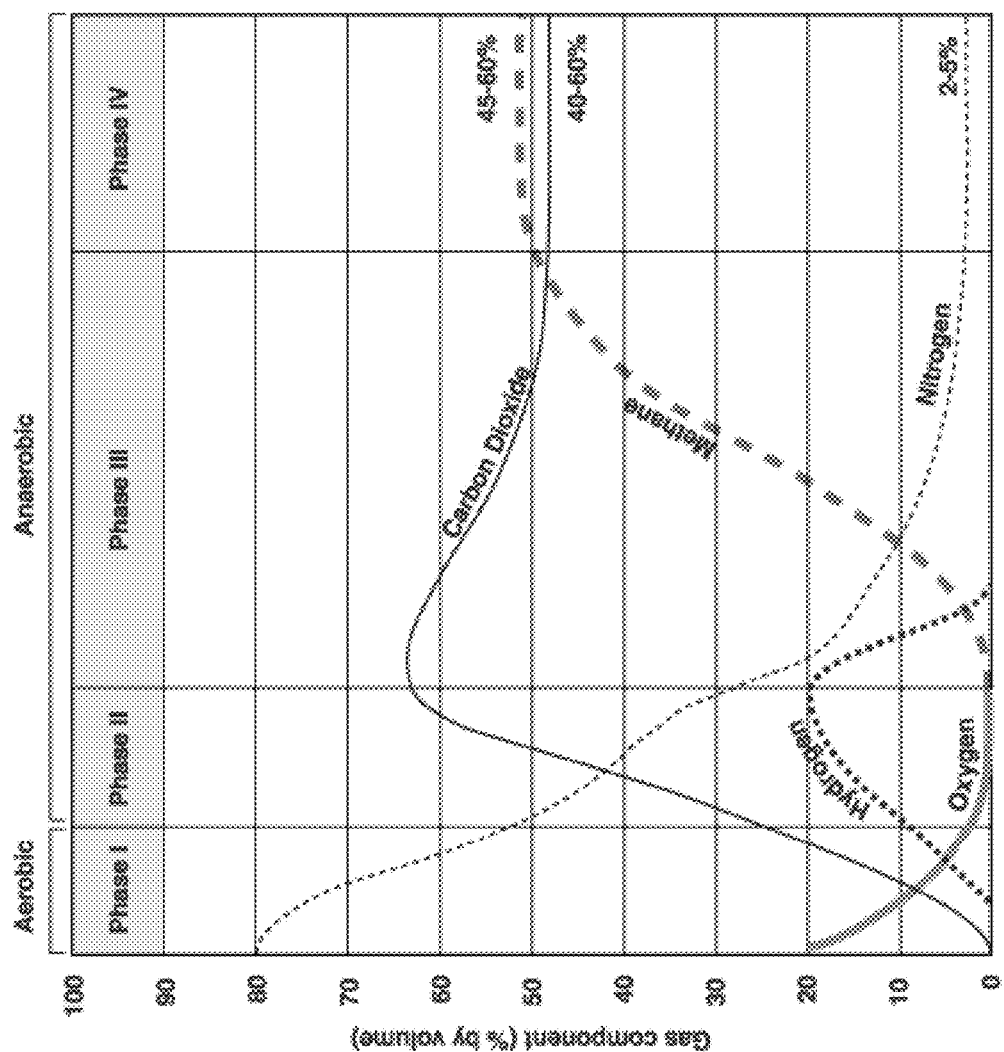
FIG. 8 is a chart that illustrates the gas production in a landfill at various phases of the landfill.

Referring now to FIG. 5, there is illustrated a control unit 400 of the portable monitor 100. Control unit 400 is a portable handheld device that is used to a) at least partially control the operation of measuring unit 200; b) obtain information, process information obtained/measured by the measuring unit 200, and/or c) monitor the operation of the measuring unit 200. As can be appreciated, control unit 400 can have other or additional uses. The communication between control unit 400 and measuring unit 200 is typically wireless; however, a cable connection using a cable can be optionally used to connect together the control unit and the measuring unit.

Control unit 400 is typically sized and configured like a smartphone, typical PDA device, Palm PC device or Black-Berry® device, virtual reality device, or augmented reality device; however, the control unit can be sized and configured in other ways. These types of devices are desirable due to their small, lightweight, and rugged configuration. The housing 402 of the control unit is made of a durable material that protects the internal components of control unit 400 from damage. A protective material 404 can be positioned about all or a portion of the top, bottom, and side edges of the housing to provide additional protection to the housing; however, this is not required. The protective material can be formed of rubber, plastic, foam, etc. Generally, protective material 404 is a durable and flexible material that can absorb a force that is applied to housing 402, such as an object bumping into the housing or the control unit being dropped on the ground. Control unit 400 is configured to be used in a wide variety of environments. Control unit 400 typically has an Ingress Protection Rating of at least IP67. The control unit is typically configured to operate in temperatures as low as about −20° F., and as high as about 140° F. The control unit typically has a weight and size that is less than the measuring unit. Typically, the control unit has a weight of less than about 1.5 lbs., and a volume of less than about 75 cubic in.

The top face 410 of the housing of the control unit optionally includes a display screen 420 (LED display, VGA display, QLED display, Plasma display, AMOLED display, etc.). Display screen 420 may be a black and white or a color display. The display screen may or may not be a touch screen. The display screen is configured to enable an operator to view various types of information. Display screen 420 may include touch screen features to enable an operator to a) enter information into the control unit, b) access information from the control unit, c) access information from the measuring unit, and/or d) send information to the measuring unit; however, this is not required. A stylus pen or the like (not shown) may be used with the touch screen features of the display to facilitate in the operation of the control unit; however, this is not required. The top face of the control unit also includes several buttons 430 to operate one or more functions/features of the control unit (e.g., power on/off button, cursor button, function button, enter button, delete button, text buttons, character buttons, numeric buttons, etc.). Control unit 400 may also include a display protector (not shown) that is removably fitted over the display screen to protect the display screen from damage; however, this is not required. The control unit can also include a hand strap and/or clip connector to facilitate in the carrying of the control unit; however, this is not required.

Control unit 400 can optionally include one or more speakers, microphones, power connectors, communication ports, memory slots, scanners, cameras, and the like; however, this is not required.

Control unit 400 includes one or more circuits and/or microprocessors to operate one or more software and/or hardware programs that are loaded in the control unit. For example, the control unit may include one or more processors in combination with various amounts of data storage memory. An operating system (e.g., Microsoft Windows Mobile software or the like) can optionally be loaded in the control unit. Various other types of software/firmware can be loaded in the control unit to enhance the features/operation of the control unit. Such software can include, but is not limited to, GPS software, navigation software, wireless communication software, photograph/video software, sound/music software, sound recording software, file/data transfer software, internet browser software, word processor software, touch screen software, database software, spreadsheet software, email software, calendar software, address book software, security software, data management software, Microsoft Office software, Android software, Linux software, JAVA software, printer software, photo software, operating system software, PDF software, security software, image modification software, active sync software, address books, clock, calendar, scanning software, camera software, voice recognition software, internet browser, phone software, and the like. Control unit 400 also includes software/firmware used to 1) calibrate, diagnose problems, control, and/or monitor the measuring unit, and/or 2) receive and/or transmit information between the control unit and measuring unit. Control unit 400 may also include software/firmware to process the information received from the measuring unit to provide additional information about the landfill well. The control unit optionally includes wireless technology to transfer information between the control unit and the measuring unit (e.g., 802.11 wireless technology, Bluetooth® technology, IR technology, etc.). The control unit can optionally include other optional components such as, but not limited to, camera, microphone, speaker, indicators (e.g., battery level indicator, on/off indicator, etc.), power pack compartment to store one or more rechargeable energy cells, one or more connection ports (e.g., fire wire, USB, serial cable, phone cable, ethernet cable, etc.), and/or one or more expansion slots (e.g., Type 1 and/or Type II expansion slots), etc.

In operation, control unit 400 can be used to control most, if not all, of the operations of the measuring unit once the measuring unit has been connected to the landfill well. As such, an operator is able to remotely monitor and/or control the measuring unit. This is a significant improvement over prior art portable monitors wherein the operator had to be positioned next to the single portable monitor in order to monitor the operation of the single portable monitor, control the operation of the single portable monitor, and to take measurements from the single portable monitor.

Control unit 400 can optionally be configured to connect wirelessly to the measuring unit; however, a cable connection can be used. Control unit 400 typically includes GPS hardware and software. The GPS feature can guide a user to a particular landfill and/or to a particular landfill well. Control unit 400 can optionally include a scanner such a bar code reader. The scanner can be used to scan information on a landfill well (e.g., bar code, etc.) to verify the identity of a landfill well and/or landfill location. In one application, the scanning of an identity label on a landfill well enables the control unit to call up past information regarding the landfill well and/or landfill site (e.g., landfill information, past landfill results, notes about landfill, etc.). Also or alternatively, control unit 400 can optionally include RFID hardware and software to detect and RFID tag on the landfill well and/or landfill site. Similar to the identity label, the RFID tag can enable control unit 400 to call up past information regarding the landfill well and/or landfill site.

The control unit can include a camera to take pictures of a landfill well and/or landfill site. Such pictures can be optionally stored in the control unit and be associated with the file for a particular landfill well and/or landfill site.

Control unit 400 can optionally include a cellular modem to enable the control unit to make and receive calls and/or to connect to the internet. The control unit may include one or more connectors that enable the control unit to connect to an ethernet connection for connection to the internet. The cellular and/or internet connection can be used to send and/or receive various types of information (e.g., updates, software fixes, download/upload data between control unit and another device, etc.).

Control unit 400 optionally includes gas analyzer software to 1) process data received from the measuring unit regarding the fluid flow from the well (e.g., fluid composition, etc.), and/or 2) control and/or monitor the operations of the measuring unit.

Generally, for each landfill well that is tested, control unit 400 can optionally be configured to require that the user name be entered, and the date and time the test occurred. This information is stored in the memory of the control unit and is associated with a particular landfill well.

Control unit 400 optionally includes calibration software to calibrate the pressure sensors and/or the chemical analyzers in the measuring unit. Generally, the chemical analyzers and pressure sensors should be calibrated prior to each landfill well being tested. A calibration gas is generally used to calibrate one or more of the chemical analyzers in the measuring unit.

The identity of a landfill well that is stored in the control unit can optionally be labeled by at least three different methods, namely, manual inputted information, GPS location, and/or RFID tag or some other identity label. Control unit 400 can include software to search for a landfill well in memory using one or more of these labeling methods.

Control unit 400 optionally includes software/firmware that creates a display on the display screen to provide information on the progress of the analyzing of the landfill well. Generally, the display screen will identify the name or identity of the landfill well and information about the fluid flowing from the well (e.g., well temperature, various pressures from the well, chemical analysis of one or more components of the fluid from the well, LEL, UEL, pump status, etc.); however, this is not required. For example, one screen display may provide information about 1) the presence/amount of methane, 2) the presence/amount of carbon dioxide, 3) the presence/amount of oxygen, 4) the presence/amount of carbon monoxide, 5) the presence/amount of hydrogen, and/or 6) the presence/amount of hydrogen sulfide. The same screen display may optionally provide additional information regarding a) balance amount of other fluid components (e.g., 100%—vol. % methane, —vol. % oxygen, —vol. % carbon dioxide, —vol. % hydrogen), b) methane to carbon dioxide ratio, c) balance amount of other fluid components to oxygen ratio, d) fluid temperature, e) ambient temperature, f) pump running status, g) available pressure, h) applied pressure, i) differential pressure, j) fluid filter status, k) chemical analyzer status, and/or l) flow rate of fluid into measuring unit. As can be appreciated, measured values can optionally be presented on more than one screen display. In such an arrangement, the user can optionally toggle between two of more display screens to cause a particular display to show on the display screen. In one specific arrangement, one screen display can include information about 1) the name or identity of the landfill well, 2) the presence/amount of methane, 3) the presence/amount of carbon dioxide, and 4) the presence/amount of oxygen; and another screen display can include information about a) the name or identity of the landfill well, b) the available pressure of the well, c) applied pressure of the well, and d) the differential pressure of the well. Additional screen displays can optionally include information about past test results of the landfill well so that the user can compare present readings to previous readings. Such historical information can be used by the user to adjust the well as required.

Control unit 400 can optionally include software/firmware that facilitates in providing warnings to a user and/or identifying information that is not within some predefined acceptable ranges. For example, if a) the LEL and/or UEL levels for a landfill well, b) balance of gas value, c) ratio of balance gas to oxygen value, d) ratio of methane to carbon dioxide value, d) one or more pressure values are equal to or outside some predefined limit, e) filter expired and/or needs to be replaced, and/or f) chemical analyzer is damaged, contaminated, and/or needs to be replaced. Control unit 400 can optionally cause such warnings to be displayed in an enhanced manner (e.g., different font, different color, larger font, flashing or blinking value, etc.), display a warning message, and/or cause some audible signal to occur. For example, when the ratio of balanced gas to oxygen value is near or below 4, such a value can indicate an air leak in a testing hose, in the well, and/or the need to recalibrate or replace a chemical analyzer. Also, when the ratio of methane to carbon dioxide is lower than 1.1, such a ratio may indicate that stress conditions exist in the landfill and the fluid flow through the well rate may need to be adjusted. The ratio may also provide information on the different phases of landfill gas production for a particular landfill well. The software used in control unit 400 can optionally enable a user to set or adjust one or more of the predefined values. Such predefined values can be customized for different landfill wells or other types of testing locations; however, this is not required.

Control unit 400 can optionally include software/firmware that enables the user to provide additional information about a particular landfill well or testing location. Such information can include, but is not limited to, name of landfill site, name of landfill well, landfill address, GPS location of landfill site, GPS location of landfill well, bar code information, RFID information, landfill well type (e.g., pitot tube, orifice tube, S pitot tube, etc.), pipe size (e.g., 0.5, 1, 1.5, 2, 3, 4, 6, 8, etc.) and/or plate size (e.g., 0.25, 0.5, 1, 1.24, 1.5, 1.75, etc.).

Control unit 400 can optionally include software to determine if data for one or more landfill wells was not obtained or fully obtained and/or input during a certain predefined testing interval. This feature can be used to ensure that all landfill wells are fully and timely monitored. Many landfill wells are generally not monitored on a daily basis. For landfills that require constant or daily monitoring, portable monitors are typically not used. Permanent monitoring systems are generally set up for such landfill wells. For landfill wells that only require periodic monitoring (e.g., landfill well that require monitoring no more than once a week), a portable monitor in accordance with the present disclosure is generally used. The portable monitor is configured to be temporarily connected to a landfill well, conduct the landfill well test, disconnected from the landfill well, and then moved to another landfill well to test such well. This testing cycle is repeated to test multiple landfill wells.

The software/firmware used by control unit 400 can be configured to interface with software on another device (e.g., network computer, tablet computer, laptop computer, desktop computer, smartphone, PDA, virtual reality device, augmented reality device, etc.) to enable transfer of data between the control unit and such other devices. Such communication can be wireless, cable connection, etc. Sync software on the control unit can optionally be used to facilitate in such communication with other devices.

The software/firmware on control unit 400 can provide the user with various types of warnings (e.g., error codes, visual warnings, audible warnings, etc.) to inform the user that attention may be required during a certain procedure. The software can also optionally provide warning errors to provide the user about the status of one or more components of the portable monitor and/or the manner in which the portable monitor is connected to a landfill well and/or one or more devices. Examples of errors include:

1) Battery Failure—The battery gauge is displaying erroneous battery data, as a result of a charging chip failure. Such a failure may affect battery cut-offs and accurate monitoring;
2) Charging Failure—The charging chip is not shutting off the charging process;
3) Charging Chip Failure—The charging chip is not maintaining a charge rate, which makes the charging process longer;
4) Sensor Failure—The pump, manifold pressure sensor, or any of the chemical sensors, temperature sensors, one or more pressure sensors have stopped operating correctly, are not drawing any electric current, and providing incorrect values;
5) Excessive Current Draw—Any number of parts may have failed due to a short or component failure;
6) Pressure Sensor Failure—One of the pressure sensors is reading out of spec, likely due to an overpressure situation (blown sensor);
7) Low Flow Condition—Improper fluid flow to the measuring unit;
8) Oxygen Sensor Failure—Oxygen sensor is out of specification;
9) Over Pressure error—Pressure applied to pressure sensors is higher than the sensors are specified for;
10) Battery low Error—Battery charge level is low;
11) Temperature Error—Measurement unit is too hot or too cold;
12) Connection Error—Control unit did not properly connect to the measuring unit;
13) Connection Lost—Control unit lost connection with the measuring unit;
14) Scanner Initialization Error—The scanner function is not active on the control unit;
15) GPS Error—The GPS function is not active on the control unit or the GPS has not yet connected with the satellites; and
16) Failed to find GPS/Barcode match—The GPS function or barcode reader is not active on the control unit.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

To aid the Patent Office and any readers of this application and any resulting patent in interpreting the claims appended hereto, Applicant does not intend any of the appended claims or claim elements to invoke 35 U.S.C. 112(f) unless the words "means for" or "step for" are explicitly used in the particular claim.

It will thus be seen that the objects set forth above, among those made apparent from the preceding description, are efficiently attained, and since certain changes may be made in the constructions set forth without departing from the spirit and scope of the disclosure, it is intended that all matter contained in the above description and shown in the accompanying drawings shall be interpreted as illustrative and not in a limiting sense. The disclosure has been described with reference to preferred and alternate embodiments. Modifications and alterations will become apparent to those skilled in the art upon reading and understanding the detailed discussion of the disclosure provided herein. This disclosure is intended to include all such modifications and alterations insofar as they come within the scope of the present disclosure. It is also to be understood that the following claims are intended to cover all of the generic and specific features of the disclosure herein described and all statements of the scope of the disclosure, which, as a matter of language, might be said to fall there between. The disclosure has been described with reference to the certain embodiments. These and other modifications of the disclosure will be obvious from the disclosure herein, whereby the foregoing descriptive matter is to be interpreted merely as illustrative of the disclosure and not as a limitation. It is intended to include all such modifications and alterations insofar as they come within the scope of the appended claims.

What is claimed:

1. A handheld portable monitor that is configured to obtain and/or measure one or more properties of fluid at a test site; said handheld portable monitor is configured to enable a user to carry said handheld portable monitor to a test site to be tested and to enable the user to monitor and/or obtain information about one or more properties of the fluid at the test site; said handheld portable monitor is configured to enable the user to carry said handheld portable monitor from the test site; said handheld portable monitor having a total weight of less than 20 pounds and a total volume of less than 500 cubic inches; said handheld portable monitor including one or more fluid connectors that enable said handheld portable monitor to test fluid at the test site and thereafter enable said handheld portable monitor to be removed from the test site after completion of testing; said handheld portable monitor including a sensor system to obtain and/or to measure one or more properties of the fluid located at the test site; said sensor system including a) first and second sample paths and b) a valve system that controls fluid flow between said first and second sample paths; a first sensor arrangement is connected to said first sample path; a second sensor arrangement is connected to said second sample path; said first sensor arrangement includes a first hydrogen sensor; said valve system including a path valve; and wherein said valve system causing said path valve to allow the test fluid to flow through said first sample path when a hydrogen content in the test fluid is at least partially determined by said first hydrogen sensor to be at or above a predetermined level; and wherein said valve system causing said path valve to redirect the test fluid to flow through said second sample path after the hydrogen content in the test fluid is at least partially determined by said first hydrogen sensor to be below said predetermined level.

2. The handheld portable monitor as defined in claim 1, wherein said second sensor arrangement includes one or more sensors selected from the group consisting of a second hydrogen sensor, a $H_2S$ sensor, and a CO sensor.

3. The handheld portable monitor as defined in claim 1, wherein said first sensor arrangement further includes one or more sensors selected from the group consisting of a $CH_4$ sensor, an oxygen sensor, and a $CO_2$ sensor.

4. The handheld portable monitor as defined in claim 2, wherein said first sensor arrangement further includes one or more sensors selected from the group consisting of a $CH_4$ sensor, an oxygen sensor, and a $CO_2$ sensor.

5. The handheld portable monitor as defined in claim 2, wherein said second sensor arrangement includes said second hydrogen sensor; said second hydrogen sensor configured to detect lower levels of hydrogen in the test fluid than said first hydrogen sensor in said first sensor arrangement.

6. The handheld portable monitor as defined in claim 4, wherein said second sensor arrangement includes said second hydrogen sensor; said second hydrogen sensor configured to detect lower levels of hydrogen in the test fluid than said first hydrogen sensor in said first sensor arrangement.

7. The handheld portable monitor as defined in claim 5, wherein said second sensor arrangement includes said $H_2S$ sensor and a $H_2S$ filter; said $H_2S$ sensor positioned upstream from said second hydrogen sensor; said $H_2S$ filter configured to at least partially remove $H_2S$ from the test fluid as the test fluid passes through said $H_2S$ filter; said $H_2S$ filter positioned between said $H_2S$ sensor and said second hydrogen sensor.

8. The handheld portable monitor as defined in claim 6, wherein said second sensor arrangement includes said $H_2S$ sensor and a $H_2S$ filter; said $H_2S$ sensor positioned upstream from said second hydrogen sensor; said $H_2S$ filter configured to at least partially remove $H_2S$ from the test fluid as the test fluid passes through said $H_2S$ filter; said $H_2S$ filter positioned between said $H_2S$ sensor and said second hydrogen sensor.

9. The handheld portable monitor as defined in claim 1, further including a fluid component adjustment system configured to adjust a determined component content of the test fluid based on A) one or more physical properties of the test fluid and/or B) a component content of one or more components of the test fluid that have been at least partially determined by said first sensor arrangement and/or said second sensor arrangement; said fluid component adjustment system including one or more of i) $H_2/CH_4$, $H_2/CO$, $H_2/H_2S$, and/or $H_2S/CO$ concentration correction tables, ii) $H_2/CH_4$, $H_2/CO$, $H_2/H_2S$, and/or $H_2S/CO$ correction curves, and/or iii) $H_2/CH_4$, $H_2/CO$, $H_2/H_2S$, and/or $H_2S/CO$ equations.

10. The handheld portable monitor as defined in claim 8, further including a fluid component adjustment system configured to adjust a determined component content of the test fluid based on A) one or more physical properties of the test fluid and/or B) a component content of one or more components of the test fluid that have been at least partially determined by said first sensor arrangement and/or said second sensor arrangement; said fluid component adjustment system including one or more of i) $H_2/CH_4$, $H_2/CO$, $H_2/H_2S$, and/or $H_2S/CO$ concentration correction tables, ii) $H_2/CH_4$, $H_2/CO$, $H_2/H_2S$, and/or $H_2S/CO$ correction curves, and/or iii) $H_2/CH_4$, $H_2/CO$, $H_2/H_2S$, and/or $H_2S/CO$ equations.

11. The handheld portable monitor as defined in claim 9, wherein said fluid component adjustment system is configured to provide a corrected $H_2$ and/or CO concentration values based on measured $H_2$, $CH_4$, CO, and/or $H_2S$ in the test fluid.

12. The handheld portable monitor as defined in claim 10, wherein said fluid component adjustment system is configured to provide a corrected $H_2$ and/or CO concentration values based on measured $H_2$, $CH_4$, CO, and/or $H_2S$ in the test fluid.

13. The handheld portable monitor as defined in claim 9, wherein said one or more physical properties of the test fluid includes test fluid temperature and/or test fluid pressure.

14. The handheld portable monitor as defined in claim 12, wherein said one or more physical properties of the test fluid includes test fluid temperature and/or test fluid pressure.

15. The handheld portable monitor as defined in claim 1, including wireless technology to enable said handheld portable monitor to communicate with one or more remote systems selected from the group consisting of the internet, mobile phone systems, network computers, tablet computers, laptop computers, desktop computers, PDAs, and one or more separated components of said handheld portable monitor that are located remotely from one another.

16. The handheld portable monitor as defined in claim 1, including GPS software and hardware for obtaining GPS coordinates for the test site to be tested or that has been tested.

17. The handheld portable monitor as defined in claim 1, wherein said handheld portable monitor includes a RFID detection system and/or a barcode scanning system that is used to identify the tested test site.

18. The handheld portable monitor as defined in claim 1, wherein said handheld portable monitor includes a handheld portable control unit and a handheld portable measuring unit; each of said handheld portable control unit and said handheld portable measuring unit are contained in separate housings; said handheld portable control unit is configured to monitor and/or control one or more functions of said handheld portable measuring unit; said handheld portable measuring unit is configured to be removably positioned at the test site; said handheld portable control unit is configured to be physically removed from the test site after completion of the testing of the test site; said housing of said handheld portable measuring unit at least partially contains said first sensor arrangement and said second sensor arrangement; said handheld portable control unit is configured to not be required to be physically connected to the test site that is being tested while said handheld portable measuring unit is removably positioned at the test site during testing of the test site; said handheld portable measuring unit has a weight of less than 10 pounds and a volume of less than 300 cubic inches; said handheld portable control unit has a weight of less than 5 pounds and a volume of less than 100 cubic inches.

19. A method for using a handheld portable monitor to obtain and/or measure one or more properties of fluid at a test site, said method comprising:
  a. providing said handheld portable monitor; said handheld portable monitor is configured to enable a user to carry said handheld portable monitor to a test site to be tested and to enable the user to monitor and/or obtain information about one or more properties of the fluid at the test site; said handheld portable monitor is configured to enable the user to carry said handheld portable monitor from the test site; said handheld portable monitor having a total weight of less than 20 pounds and a total volume of less than 500 cubic inches; said handheld portable monitor including one or more fluid connectors that enable said handheld portable monitor to test fluid at the test site and thereafter enable said handheld portable monitor to be removed from the test site after completion of testing; said handheld portable monitor including a sensor system to obtain and/or to measure one or more properties of the fluid located at the tested test site; said sensor system including a) first and second sample paths and b) a valve system that controls fluid flow between said first and second sample paths; a first sensor arrangement is connected to said first sample path; a second sensor arrangement is connected to said second sample path; said first sensor arrangement includes a first hydrogen sensor; said valve system including a path valve;
  b. removably connecting said handheld portable monitor to said test site; and
  c. measuring/determining one or more components of the test fluid at the test site; and wherein said valve system causing said path valve to allow the test fluid to flow through said first sample path when a hydrogen content in the test fluid is at least partially determined by said first hydrogen sensor to be at or above a predetermined level; and wherein said valve system causing said path valve to redirect the test fluid to flow through said second sample path after the hydrogen content in the test fluid is at least partially determined by said first hydrogen sensor to be below said predetermined level.

20. The method as defined in claim 19, further including the step of adjusting a determined component content of the test fluid based on A) one or more physical properties of the test fluid and/or B) a component content of one or more components of the test fluid that have been at least partially determined by said first sensor arrangement and/or said second sensor arrangement; said step of adjusting a determined component content including use of one or more of i) $H_2/CH_4$, $H_2/CO$, $H_2/H_2S$, and/or $H_2S/CO$ concentration correction tables, ii) $H_2/CH_4$, $H_2/CO$, $H_2/H_2S$, and/or $H_2S/CO$ correction curves, and/or iii) $H_2/CH_4$, $H_2/CO$, $H_2/H_2S$, and/or $H_2S/CO$ equations.

* * * * *